(12) United States Patent
Conley et al.

(10) Patent No.: US 8,946,219 B2
(45) Date of Patent: Feb. 3, 2015

(54) COMBINATION THERAPY WITH A COMPOUND ACTING AS A PLATELET ADP RECEPTOR INHIBITOR

(75) Inventors: Pamela B. Conley, Palo Alto, CA (US); Patrick Andre, San Mateo, CA (US); Uma Sinha, San Francisco, CA (US)

(73) Assignee: Portola Pharmaceuticals, Inc., South San Francisco, CA (US)

( * ) Notice: Subject to any disclaimer, the term of this patent is extended or adjusted under 35 U.S.C. 154(b) by 1142 days.

(21) Appl. No.: 12/908,837

(22) Filed: Oct. 20, 2010

(65) Prior Publication Data
US 2011/0033459 A1 Feb. 10, 2011

Related U.S. Application Data

(63) Continuation of application No. 12/114,706, filed on May 2, 2008, now abandoned.

(60) Provisional application No. 60/915,649, filed on May 2, 2007, provisional application No. 60/915,911, filed on May 3, 2007, provisional application No. 60/947,921, filed on Jul. 3, 2007, provisional application No. 60/978,700, filed on Oct. 9, 2007.

(51) Int. Cl.
| | | |
|---|---|---|
| *A01N 43/58* | (2006.01) | |
| *A61K 31/50* | (2006.01) | |
| *A01N 43/54* | (2006.01) | |
| *C07D 239/42* | (2006.01) | |
| *C07D 401/04* | (2006.01) | |
| *C07D 471/04* | (2006.01) | |
| *C07D 471/22* | (2006.01) | |
| *A61K 31/505* | (2006.01) | |
| *A01N 43/06* | (2006.01) | |
| *A61K 31/38* | (2006.01) | |
| *A01N 43/02* | (2006.01) | |
| *A01N 43/12* | (2006.01) | |
| *A61K 31/422* | (2006.01) | |
| *A61K 31/235* | (2006.01) | |
| *A61K 31/435* | (2006.01) | |
| *A61K 31/517* | (2006.01) | |
| *A61K 38/48* | (2006.01) | |
| *A61K 45/06* | (2006.01) | |
| *A61K 31/4545* | (2006.01) | |

(52) U.S. Cl.
CPC ............. *A61K 31/422* (2013.01); *A61K 31/235* (2013.01); *A61K 31/435* (2013.01); *A61K 31/517* (2013.01); *A61K 38/4846* (2013.01); *A61K 45/06* (2013.01); *A61K 31/4545* (2013.01)

USPC ........... 514/247; 514/256; 514/257; 514/269; 514/430; 514/438; 514/443

(58) Field of Classification Search
CPC ..... A61K 31/10; A61K 31/17; A61K 31/381; A61K 31/495
USPC ......... 514/183, 247, 256, 257, 269, 430, 438, 514/443
See application file for complete search history.

(56) References Cited

U.S. PATENT DOCUMENTS

| | | |
|---|---|---|
| 6,376,515 B2 | 4/2002 | Zhu et al. |
| 6,509,348 B1 | 1/2003 | Olgetree |
| 6,835,739 B2 | 12/2004 | Zhu et al. |
| 6,844,367 B1 | 1/2005 | Bing-Yan et al. |
| 7,022,695 B2 | 4/2006 | Bing-Yan et al. |
| 7,285,565 B2 | 10/2007 | Bing-Yan et al. |
| 7,312,325 B2 | 12/2007 | Bing-Yan et al. |
| 7,314,874 B2 | 1/2008 | Bing-Yan et al. |
| 7,342,013 B2 | 3/2008 | Bing-Yan et al. |
| 7,727,981 B2 | 6/2010 | Bing-Yan et al. |
| 7,767,697 B2 | 8/2010 | Song et al. |
| 2002/0077486 A1 | 6/2002 | Scarborough et al. |
| 2003/0109543 A1 | 6/2003 | Ogletree |
| 2006/0100193 A1 | 5/2006 | Zhu et al. |
| 2007/0112039 A1 | 5/2007 | Grant et al. |
| 2007/0123547 A1 | 5/2007 | Scarborough et al. |
| 2007/0185092 A1 | 8/2007 | Zhu et al. |
| 2007/0259924 A1 | 11/2007 | Zhu et al. |
| 2008/0153876 A1 | 6/2008 | Sinha et al. |
| 2008/0254036 A1 | 10/2008 | Sinha et al. |
| 2008/0293701 A1 | 11/2008 | Zhao et al. |
| 2009/0186810 A1 | 7/2009 | Zwaal et al. |

FOREIGN PATENT DOCUMENTS

| | | |
|---|---|---|
| WO | WO 00/47207 A1 | 8/2000 |
| WO | WO 01/19788 A2 | 3/2001 |
| WO | WO 01/40231 A1 | 6/2001 |
| WO | WO 03/011872 A1 | 2/2003 |
| WO | WO 2005/035520 A1 | 4/2005 |
| WO | WO 2006/045756 A1 | 5/2006 |
| WO | WO 2007/056219 | 5/2007 |

OTHER PUBLICATIONS

Yamazaki, et al., Thrombosis and circulation, vol. 15, No. 1, 102-105, (2007).
US 7,479,487, 1/2009, Bing-Yan et al. (withdrawn).
International Search Report, dated Dec. 12, 2008.

*Primary Examiner* — Yong Chong
(74) *Attorney, Agent, or Firm* — Sheppard Mullin Richter & Hampton LLP

(57) ABSTRACT

The present invention is directed to pharmaceutical compositions and methods of using combination therapies containing [4-(6-fluoro-7-methylamino-2,4-dioxo-1,4-dihydro-2H-quinazolin-3-yl)-phenyl]-5-chloro-thiophen-2-yl-sulfonylurea, or a pharmaceutically acceptable salt thereof, for the treatment of thrombosis diseases.

13 Claims, 17 Drawing Sheets

COMBINATION THERAPY WITH A COMPOUND ACTING AS A PLATELET ADP RECEPTOR INHIBITOR

CROSS REFERENCE TO RELATED APPLICATIONS

This application is a continuation and claims the benefit under 35 U.S.C. §120 of co-pending U.S. patent application Ser. No. 12/114,706, filed on May 2, 2008, which in turn claims the benefit under 35 U.S.C. §119(e) of U.S. Provisional Patent Application Nos. 60/915,649, filed on May 2, 2007, 60/915,911, filed on May 3, 2007, 60/947,921, filed on Jul. 3, 2007, and 60/978,700, filed on Oct. 9, 2007, all of which are hereby incorporated by reference in their entirety.

FIELD OF INVENTION

The present invention relates generally to novel compositions and methods of using a combination of a platelet ADP receptor inhibitor, [4-(6-fluoro-7-methylamino-2,4-dioxo-1,4-dihydro-2H-quinazolin-3-yl)-phenyl]-5-chloro-thiophen-2-yl-sulfonylurea (Compound A), and an anticoagulant agent or another antiplatelet agent for the treatment of thrombotic diseases. The present invention also relates to novel compositions and methods using a combination of Compound A with an anticoagulant and another antiplatelet agent for the treatment of thrombotic diseases.

BACKGROUND OF THE INVENTION

Thrombotic complications are a major cause of death in the industrialized world. Examples of these complications include acute myocardial infarction, unstable angina, chronic stable angina, transient ischemic attacks, strokes, peripheral vascular disease, preeclampsia/eclampsia, deep venous thrombosis, embolism, disseminated intravascular coagulation and thrombotic cytopenic purpura. Thrombotic and restenotic complications also occur following invasive procedures, e.g., angioplasty, carotid endarterectomy, post CABG (coronary artery bypass graft) surgery, vascular graft surgery, stent placements and insertion of endovascular devices and prostheses. It is generally thought that platelet aggregates play a critical role in these events. Blood platelets, which normally circulate freely in the vasculature, become activated and aggregate to form a thrombus with disturbed blood flow caused by ruptured atherosclerotic lesions or by invasive treatments such as angioplasty, resulting in vascular occlusion.

An important mediator of platelet activation and aggregation is ADP (adenosine 5'-diphosphate) which is released from blood platelets in the vasculature upon activation by various agents, such as collagen and thrombin, and from damaged blood cells, endothelium or tissues. Activation of ADP results in the recruitment of more platelets and stabilization of existing platelet aggregates. Adenosine nucleotides that are released following platelet activation signal through the P2 purinergic receptors on the platelet membrane (Mills, D. C. *Thromb. Haemost.* 1996, 76:835-56; Gachet, C. *Annu Rev Pharmacol Toxicol* 2006, 46:277-300). P2 receptors are classified as either ligand-gated ion channels (P2X) or G-protein coupled receptors (GPCRs) designated as P2Y receptors (Abbrachio, M. P., Burnstock, G. *Pharmacol Ther* 1994, 64:445-75). Although initially thought to mediate its effects through a single receptor (termed $P2Y_{ADP}$ (Fredholm, B. B. et al, *TIPS* 1997, 18:79-82), ADP has more recently been shown to act on platelets through two GPCRs, the $G_q$-coupled $P2Y_1$ receptor, and the $G_i$-coupled $P2Y_{12}$ receptor. The $P2Y_{12}$ receptor was identified through expression cloning (Hollopter, G. et al, *Nature* 2001, 409:202-07), and has been demonstrated to play a critical role in thrombus stability (Andre, P. et al, *J Clin Inves,* 2003, 112:398-406) and is the target of the thienopyridine drugs ticlopine and clopidogrel. ATP, on the other hand, acts through the ligand-gated channel P2X1 on platelets (Gachet, C. *Annu Rev Pharmacol Toxicol* 2006, 46:277-300).

U.S. Patent Publication US 2007/0123547, titled "[4-(6-Halo-7-substituted-2,4-dioxo-1,4-dihydro-2H-quinazolin-3-yl)-phenyl]-5-chloro-thiophen-2-yl-sulfonylureas And Forms And Methods Related Thereto," filed Nov. 3, 2006, the contents of which are incorporated herein by reference in its entirety, discloses a platelet ADP receptor inhibitor compound, [4-(6-fluoro-7-methylamino-2,4-dioxo-1,4-dihydro-2H-quinazolin-3-yl)-phenyl]-5-chloro-thiophen-2-yl-sulfonylurea, (Compound A), which has the following structure:

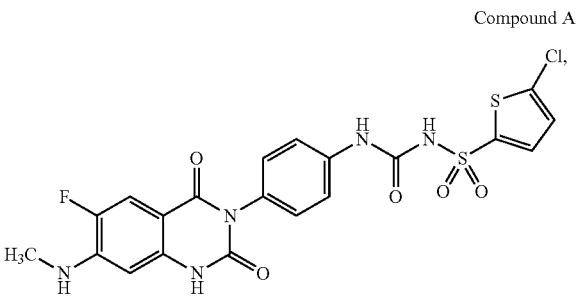 [SMILES: CNc1cc2[nH]c(=O)n(-c3ccc(NC(=O)NS(=O)(=O)c4ccc(Cl)s4)cc3)c(=O)c2cc1F]

Compound A and acts as a specific antagonist of $P2Y_{12}$.

Since treatment for diseases such as acute coronary syndrome might require coadministration of an antiplatelet agent and an anticoagulant agent, a combination would allow for increased efficacy and may provide an improved safety profile. Thus, there is a need for combination therapies combining an antiplatelet agent with an anticoagulant agent that have enhanced efficacy. There is also a need for a combination therapy that allows for lower (i.e. sub-therapeutic) dosages of each individual agent to be used in the combination which may provide an improved safety profile.

There is also a need for combination of two different antiplatelet drugs that act by different mechanisms (e.g., a $P2Y_{12}$ antagonist (Compound A) and a cox-1 inhibitor (aspirin)) in combination with an anticoagulant, as such a triple combination (clopidogrel, aspirin and heparin) is presently used in the clinic (as separate entities) during angioplasty procedures and has been found to be more efficatious than any of these drugs used alone or a combination of any two of these agents.

SUMMARY OF THE INVENTION

This invention provides methods and pharmaceutical compositions of combined therapies comprising a $P2Y_{12}$ antagonist, having the structure:

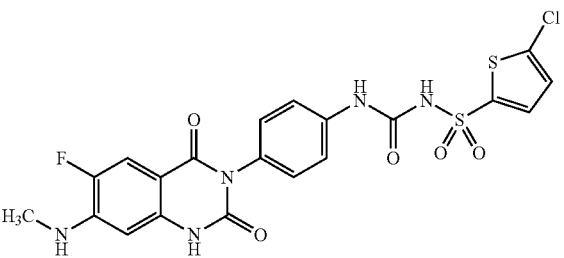 [SMILES: CNc1cc2[nH]c(=O)n(-c3ccc(NC(=O)NS(=O)(=O)c4ccc(Cl)s4)cc3)c(=O)c2cc1F]

which has the chemical name [4-(6-fluoro-7-methylamino-2,4-dioxo-1,4-dihydro-2H-quinazolin-3-yl)-phenyl]-5-chloro-thiophen-2-yl-sulfonylurea, and is referred to throughout as "Compound A".

It is contemplated based on experimental results that a combination of Compound A with an anticoagulant agent, such as a factor Xa inhibitor, and/or another antiplatelet agent, such as a cyclooxygenase inhibitor, will produce improved antithrombotic effect over any of the agents alone.

Accordingly, the present invention provides novel methods for treating a condition in a mammal characterized by undesired thrombosis, comprising administering to said mammal a therapeutically effective amount of Compound A, [4-(6-fluoro-7-methylamino-2,4-dioxo-1,4-dihydro-2H-quinazolin-3-yl)-phenyl]-5-chloro-thiophen-2-yl-sulfonylurea, or a pharmaceutically acceptable salt thereof, and a therapeutically effective amount of another therapeutic agent. The other therapeutically effective agent is selected from an anticoagulant agent, an antiplatelet agent, or combinations thereof.

In one aspect, the present invention provides a novel method for preventing or treating thrombosis and thrombosis-related conditions in a mammal comprising administering to said mammal a therapeutically effective amount of [4-(6-fluoro-7-methylamino-2,4-dioxo-1,4-dihydro-2H-quinazolin-3-yl)-phenyl]-5-chloro-thiophen-2-yl-sulfonylurea (Compound A), or a pharmaceutically acceptable salt thereof, and an anticoagulant agent. In some embodiments, the anticoagulant agent is a specific inhibitor of factor Xa, [2-({4-[(dimethylamino)iminomethyl]phenyl}carbonylamino)-5-methoxyphenyl]-N-(5-chloro(2-pyridyl))carboxamide (betrixaban, see below), or a pharmaceutically acceptable salt thereof.

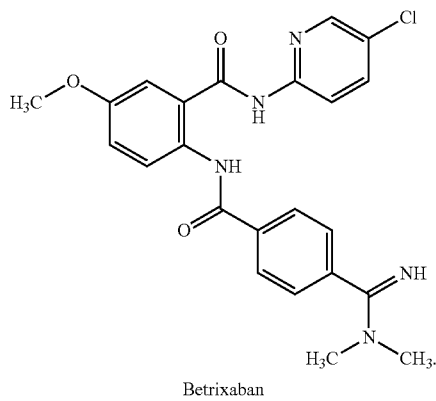 [SMILES: COc1ccc(NC(=O)c2ccc(C(=N)N(C)C)cc2)c(C(=O)Nc2ccc(Cl)cn2)c1]

Betrixaban

In another aspect, the present invention provides a novel method for preventing or treating thrombosis and/or a condition in a mammal comprising administering to said mammal a therapeutically effective amount of [4-(6-fluoro-7-methylamino-2,4-dioxo-1,4-dihydro-2H-quinazolin-3-yl)-phenyl]-5-chloro-thiophen-2-yl-sulfonylurea (Compound A), or a pharmaceutically acceptable salt thereof, and another antiplatelet agent.

In still another aspect, the present invention provides a novel method for preventing or treating thrombosis and/or a thrombosis-related condition in a mammal comprising administering to said mammal a therapeutically effective amount of Compound A or a pharmaceutically acceptable salt thereof, an anticoagulant agent and another antiplatelet agent.

The present invention also provides a novel pharmaceutical composition comprising a pharmaceutically acceptable carrier, Compound A, [4-(6-fluoro-7-methylamino-2,4-dioxo-1,4-dihydro-2H-quinazolin-3-yl)-phenyl]-5-chloro-thiophen-2-yl-sulfonylurea, or a pharmaceutically acceptable salt thereof, and a therapeutically effective amount of another therapeutic agent. The other therapeutically effective agent is selected from an anticoagulant agent, an antiplatelet agent, or combinations thereof.

In another aspect, the present invention provides a novel pharmaceutical composition comprising a pharmaceutically acceptable carrier, Compound A or a pharmaceutically acceptable salt thereof, and an anticoagulant agent. In some embodiments, the anticoagulant agent is betrixaban, or a pharmaceutically acceptable salt thereof.

In another aspect, the present invention provides a novel pharmaceutical composition comprising a pharmaceutically acceptable carrier, Compound A or a pharmaceutically acceptable salt thereof, and another antiplatelet agent.

In still another aspect, the present invention provides a novel composition comprising a pharmaceutically acceptable carrier, Compound A or a pharmaceutically acceptable salt thereof, an anticoagulant agent and another antiplatelet agent.

This invention also provides a novel kit, comprising: a first container for containing Compound A, or a pharmaceutically acceptable salt thereof, and a second container for containing another therapeutic agent selected from the group consisting of an anticoagulant agent, an antiplatelet agent other than Compound A, and combinations thereof.

These and other embodiments of the present invention are further described in the text that follows.

The compositions of this invention are contemplated to provide for a synergistic effect in one or more of the following areas: improved therapeutic results, improved safety, reduced amount to achieve equivalent efficacy of one or more of the combination drugs as compared to the amount of that drug required to achieve the same level of efficacy when used alone.

BRIEF DESCRIPTION OF THE DRAWINGS

FIG. 10 shows that Compound A delays the time for appearance of first thrombus in the intravital microscopy model. FIG. 11 shows the pharmacokinetics and pharmacodynamics (PK/PD) correlation of Compound A in delaying the time for appearance of first thrombus. FIG. 12 shows that Compound A inhibits vascular occlusion. FIG. 13 shows the PK/PD correlation of Compound A in inhibiting vascular occlusion.

FIGS. 14 and 15 show that the combination of non-effective doses of Compound A and betrixaban significantly prolongs time for appearance of first thrombus. FIGS. 16 and 17 show that the combination of non-effective doses of Compound A and betrixaban significantly inhibits of thrombosis.

DETAILED DESCRIPTION OF THE INVENTION

Figure 1:
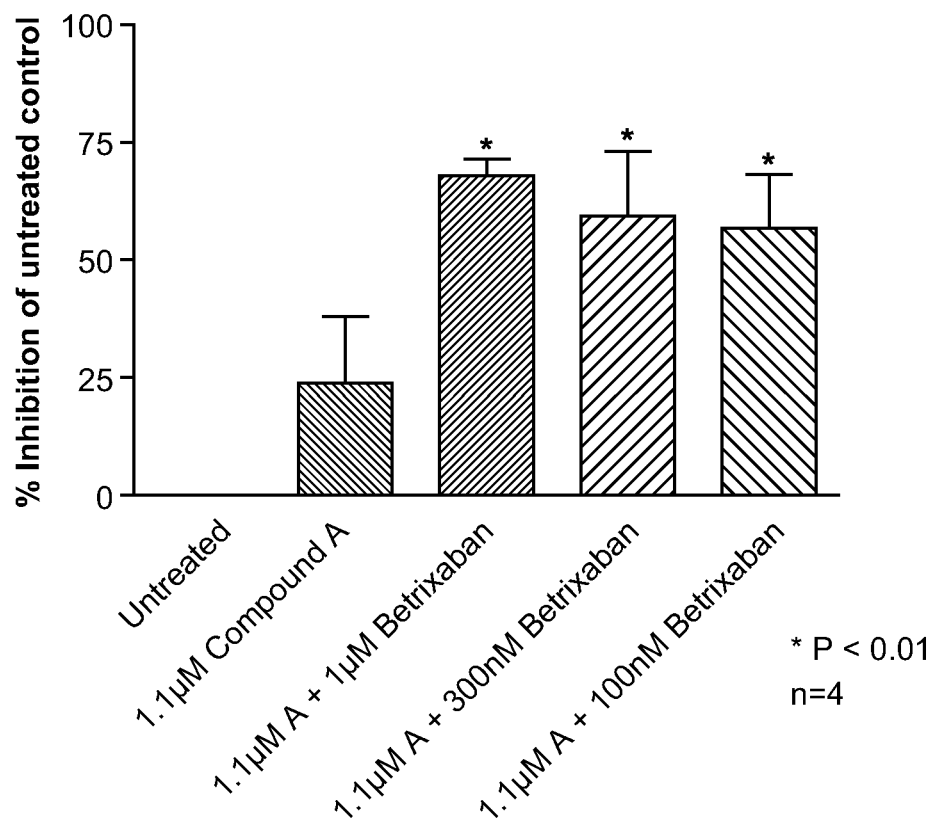
FIG. 1 shows the percent inhibition of thrombus formation by a combination of 1.1 μM of Compound A and a coagulation factor Xa inhibitor, betrixaban, in a perfusion chamber assay, where the concentration of betrixaban varies from 100 nM to 1.1 μM.

This invention relates to a method and compositions for preventing or treating thrombosis and thrombosis-related conditions in a mammal using a combination of Compound A with a co-administered agent. Prior to describing this invention in more detail, the following terms are defined.

I. Definitions

It is to be noted that as used herein and in the claims, the singular forms "a," "an" and "the" include plural referents unless the context clearly dictates otherwise. Thus, for example, reference to "a pharmaceutically acceptable carrier" in a composition includes two or more pharmaceutically acceptable carriers, and so forth.

It must be further noted that the classification of certain therapeutic agents based on their intended use or mechanisms of action is based on the general knowledge of a person skilled in the art and for classification purposes only. The purported mechanisms are not intended to be used as a limitation for the therapeutic agents unless the context clearly dictates otherwise. Some therapeutic agents may act through two or more mechanisms or are able to be used to treat two or more conditions. It is also to be understood that the particular agents given in each categories are for examples only and are not intended to limit the scope of the present invention.

"Comprising" is intended to mean that the compositions and methods include the recited elements, but do not exclude others. "Consisting essentially of" when used to define compositions and methods, shall mean excluding other elements of any essential significance to the combination for the intended use. Thus, a composition consisting essentially of the elements as defined herein would not exclude trace contaminants from the isolation and purification method and pharmaceutically acceptable carriers, such as phosphate buffered saline, preservatives, and the like. "Consisting of" shall mean excluding more than trace elements of other ingredients and substantial method steps for administering the compositions of this invention. Embodiments defined by each of these transition terms are within the scope of this invention.

The term "treatment" or "treating" means any treatment of a disease or condition in a subject, such as a mammal, including: 1) preventing or protecting against the disease or condition, that is, causing the clinical symptoms not to develop; 2) inhibiting the disease or condition, that is, arresting or suppressing the development of clinical symptoms; and/or 3) relieving the disease or condition that is, causing the regression of clinical symptoms.

As used herein, the term "preventing" refers to the prophylactic treatment of a patient in need thereof. The prophylactic treatment can be accomplished by providing an appropriate dose of a therapeutic agent to a subject at risk of suffering from an ailment, thereby substantially averting onset of the ailment.

It will be understood by those skilled in the art that in human medicine, it is not always possible to distinguish between "preventing" and "suppressing" since the ultimate inductive event or events may be unknown, latent, or the patient is not ascertained until well after the occurrence of the event or events. Therefore, as used herein the term "prophylaxis" is intended as an element of "treatment" to encompass both "preventing" and "suppressing" as defined herein. The term "protection," as used herein, is meant to include "prophylaxis."

The term "mammal" includes, without limitation, human, monkeys, rabbits, mice domestic animals, such as dogs and cats, farm animals, such as cows, horses, or pigs, and laboratory animals.

The term "condition" refers to a disease state for which the methods and compositions of the present invention are being used against.

As used herein, "thrombosis and thrombosis-related conditions" may be any of, but are not limited to the following: any thrombosis, particularly a platelet-dependent thrombotic indication, including, but not limited to, acute myocardial infarction, unstable angina, chronic stable angina, transient ischemic attacks, strokes, peripheral vascular disease, preeclampsia/eclampsia, deep venous thrombosis, embolism, disseminated intravascular coagulation and thrombotic cytopenic purpura, thrombotic and restenotic complications following invasive procedures, e.g., angioplasty, carotid endarterectomy, post CABG (coronary artery bypass graft) surgery, vascular graft surgery, stent placements and insertion of endovascular devices and prostheses, and hypercoagulable states related to genetic predisposition or cancers.

"[4-(6-Fluoro-7-methylamino-2,4-dioxo-1,4-dihydro-2H-quinazolin-3-yl)-phenyl]-5-chloro-thiophen-2-yl-sulfonylurea," or "Compound A" is intended to refer to the compound having the following structure:

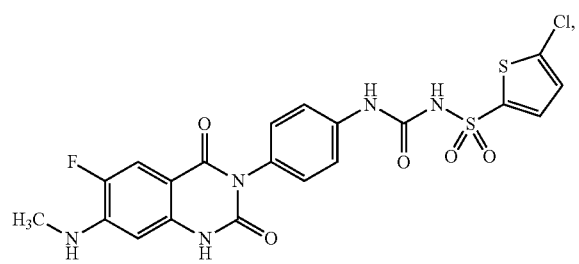 [SMILES: CNc1cc2[nH]c(=O)n(-c3ccc(NC(=O)NS(=O)(=O)c4ccc(Cl)s4)cc3)c(=O)c2cc1F]

and its tautomers.

"Therapeutically effective amount" means an amount of Compound A or the co-administered agent of the present invention that is effective to treat a target disease or condition when administered in combination. The therapeutically effective amount will vary depending upon the specific combination, the subject and disease condition being treated, the weight and age of the subject, the severity of the disease condition, the dosing regimen to be followed, timing of administration, the manner of administration and the like, all of which can be determined readily by one of ordinary skill in the art.

In some embodiments, it is contemplated that the therapeutically effective amount of Compound A or the co-administered agent in the combination can be less than their respective effective amount when used as a single agent. In this case, the therapeutically effective amount is referred to as "sub-therapeutic dosage." Thus, the term "sub-therapeutic dosage" is intended to mean a dosage that is lower than the optimal dosage for a therapeutic agent when used as a single agent, but when used in the combinations described herein, provides a therapeutic result.

"Anticoagulant agents" or "anticoagulants" are agents that prevent blood clot formation. Examples of anticoagulant agents include, but are not limited to, specific inhibitors of thrombin, factor IXa, factor Xa, factor XI, factor XIa, factor XIIa or factor VIIa, heparin and derivatives, vitamin K antagonists, and anti-tissue factor antibodies, as well as inhibitors of P-selectin and PSGL-1. Examples of specific inhibitors of thrombin include hirudin, bivalirudin (Angiomax®), argatroban, ximelagatran (Exanta®, see structure below), dabigatran (see structure below), AZD0837 (being studied in clinical trial A Controlled, Randomized, Parallel, Multi-Centre Feasibility Study of the Oral Direct Thrombin Inhibitor, AZD0837, Given as ER Formulation, in the Prevention of Stroke and Systolic Embolic Events in Patients With Atrial Fibrillation, Who Are Appropriate for But Unable/Unwilling to Take VKA Therapy with ClinicalTrials.gov Identifier: NCT00623779), RB2006 (a single-stranded, nucleic acid aptamer, by Regado Biosciences, Durham, N.C., as described in Dyke, C. K. et al., First-in-Human Experience of an Antidote-Controlled Anticoagulant Using RNA Aptamer Technology, *Circulation* 2006; 114:2490-2497), and lepirudin (Refludan®). Examples of heparin and derivatives include unfractionated heparin (UFH), low molecular weight heparin (LMWH), such as enoxaparin (Lovenox®), dalteparin (Fragmin®), and danaparoid (Organan®); and synthetic pentasaccharide, such as fondaparinux (Arixtra®), idraparinux and biotinylated idraparinux. Examples of vitamin K antagonists include warfarin (Coumadin®), phenocoumarol, acenocoumarol (Sintrom®), clorindione, dicumarol, diphenadione, ethyl biscoumacetate, phenprocoumon, phenindione, and tioclomarol.

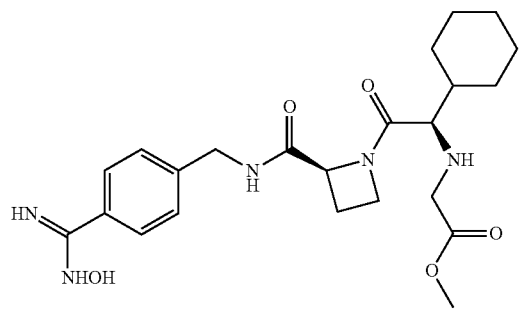

Ximelagatran

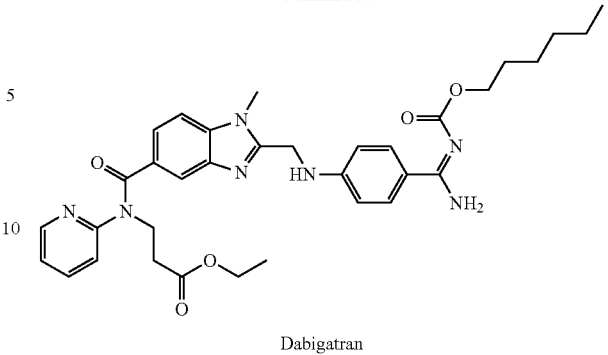

Dabigatran

The term "factor Xa inhibitors" or "inhibitors of factor Xa" refers to compounds that can inhibit the coagulation factor Xa's activity of catalyzing conversion of prothrombin to thrombin in vitro and/or in vivo. Factor Xa is an enzyme in the coagulation pathway, and is the active component in the prothrombinase complex that catalyzes the conversion of prothrombin to thromin. Thrombin is responsible for converting fibrinogen to fibrin, and leads to formation of blood clot. Thus, inhibition of factor Xa is considered to be an effective strategy of treating and preventing thrombotic disease(s). A preferred factor Xa inhibitor inhibits thrombin formation both in vitro and in vivo. A more preferred factor Xa inhibitor shows anticoagulant efficacy in vivo. The term "specific inhibitor of factor Xa" or "specific factor Xa inhibitor" is intended to refer to factor Xa inhibitors that exhibit substantially higher inhibitory activities against factor Xa than against other enzymes or receptors of the same mammal. Preferably, a specific factor Xa inhibitor does not have significant known inhibitory activity against other enzymes or receptors in the same mammal system at its therapeutically effective concentrations.

Examples of known factor Xa inhibitors include, without limitation, fondaparinux, idraparinux, biotinylated idraparinux, enoxaparin, fragmin, NAP-5, rNAPc2, tissue factor pathway inhibitor, LY517717 (by Eli Lilly & Co., Indianapolis, Ind., USA, having the structure of N-{(1R)-2-[4-(1-methyl-4-piperidinyl)-1-piperazinyl]-2-oxo-1-phenyl-ethyl}-1H-indole-6-carboxamide, as described in, e.g., A Phase II Study of the Oral Factor Xa Inhibitor LY517717 for the Prevention of Venous Thromboembolism after Hip or Knee Replacement, Agnelli G. et al, *J. Thromb. Haemost.* 2007, 5(4):746-53, studied in clinical trials, such as A Comparison of the Oral Anticoagulant LY517717 Difumarate to Subcutaneous Enoxaparin for the Prevention of Venous Thromboembolic Events (VTE) Post-Total Hip Replacement (THR) and Post-Total Knee Replacement (TKR) Surgery, with ClinicalTrials.gov Identifier: NCT00074828), YM-150 (as described in e.g., Eriksson, B. I. et al, *J. Thromb. Haemost.* 2007, 5:1660-65, and studied in clinical trials, such as Direct Factor Xa Inhibitor YM150 for Prevention of Venous Thromboembolism in Patients Undergoing Elective Total Hip Replacement. A Double Blind, Parallel, Dose-Finding Study in Comparison With Open Label Enoxaparin with ClinicalTrials.gov Identifier: NCT00353678), Daiichi DU-176b (as described in, e.g., E. Hylek, DU-176b, An Oral, Direct Factor Xa Antagonist, *Current Opinion in Investigational Drugs* 2007 8:778-783 and studied in clinical trials, such as, A Phase IIb, Randomized, Parallel Group, Double-Blind, Double-Dummy, Multi-Center, Multi-National, Multi-Dose, Study of DU-176b Compared to Dalteparin in Patients Undergoing Elective Unilateral Total Hip Replacement with ClinicalTrials.gov Identifier: NCT00398216), betrixaban (as described below), and compounds listed in Table 1, and derivatives thereof.

TABLE 1

| Structure | Chemical Name | |
|---|---|---|
| 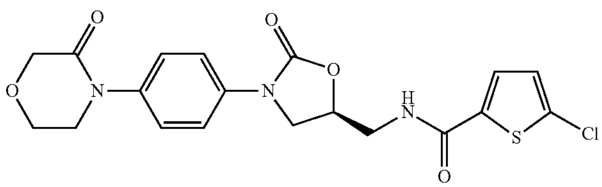 [SMILES: O=C(NC[C@H]1CN(c2ccc(N3CCOCC3=O)cc2)C(=O)O1)c1ccc(Cl)s1] | (5S)-5-chloro-N-((2-oxo-3-(4-(3-oxomorpholino)phenyl)oxazolidin-5-yl)methyl)thiophene-2-carboxamide | Rivaroxaban, as described in, e.g., Turpie, A. G., et al, J. Thromb. Haemost. 2005, 3(11): 2479-86 |
| 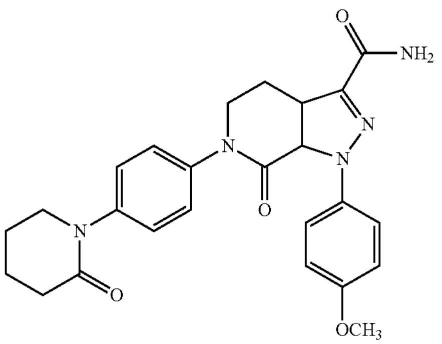 [SMILES: COc1ccc(N2N=C(C(N)=O)C3CCN(c4ccc(N5CCCCC5=O)cc4)C(=O)C32)cc1] | 1-(4-methoxyphenyl)-7-oxo-6-(4-(2-oxopiperidin-1-yl)phenyl)-3a,4,5,6,7,7a-hexahydro-1H-pyrazolo[3,4-c]pyridine-3-carboxamide | Apixaban |
| 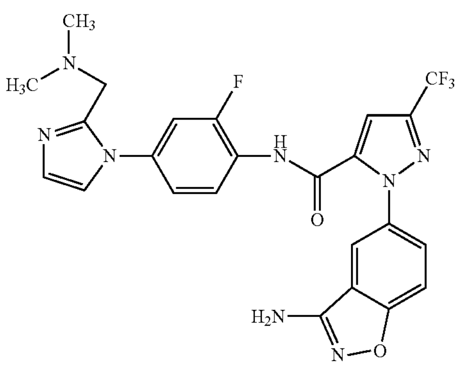 [SMILES: CN(C)Cc1nccn1-c1ccc(NC(=O)c2cc(C(F)(F)F)nn2-c2ccc3onc(N)c3c2)c(F)c1] | 1-(3-aminobenzo[d]isoxazol-5-yl)-N-(4-(2-((dimethylamino)methyl)-1H-imidazol-1-yl)-2-fluorophenyl)-3-(trifluoromethyl)-1H-pyrazole-5-carboxamide | Razaxaban |
| 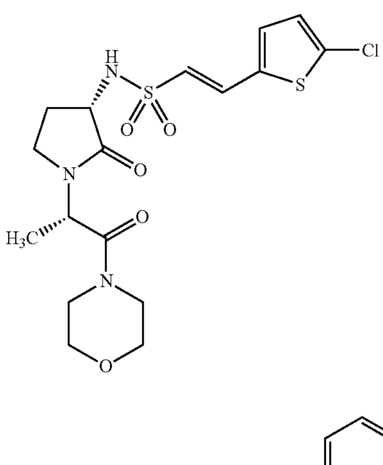 | (E)-2-(5-chlorothiophen-2-yl)-N-((S)-1-((S)-1-morpholino-1-oxopropan-2-yl)-2-oxopyrrolidin-3-yl)ethenesulfonamide | |
| 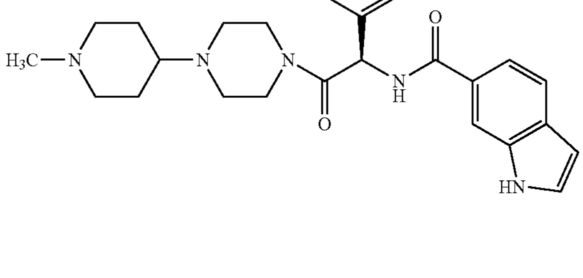 | (R)-N-(2-(4-(1-methylpiperidin-4-yl)piperazin-1-yl)-2-oxo-1-phenylethyl)-1H-indole-6-carboxamide | as described in, e.g., Agnelli, G., et al, J. Thromb. Haemost. 2007 5(4): 746-53 |

TABLE 1-continued

| Structure | Chemical Name | |
|---|---|---|
| 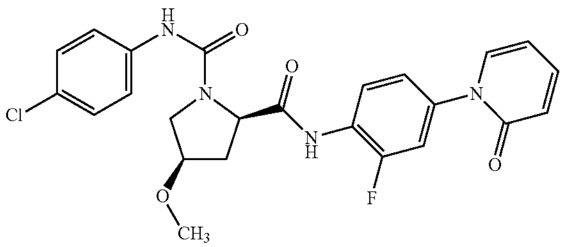 [SMILES: CO[C@@H]1C[C@H](C(=O)Nc2ccc(-n3ccccc3=O)cc2F)N(C(=O)Nc2ccc(Cl)cc2)C1] | (2R,4R)-N1-(4-chlorophenyl)-N2-(2-fluoro-4-(2-oxopyridin-1(2H)-yl)phenyl)-4-methoxypyrrolidine-1,2-dicarboxamide | as described in, e.g., Pipeline Insight: Antithrombotics-Reaching the Untreated Prophylaxis Market, 2007 |
| 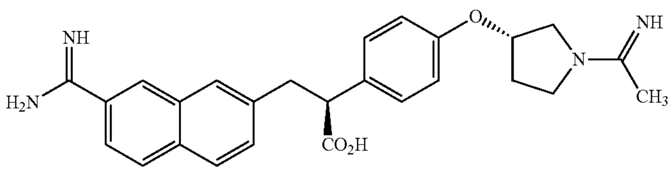 [SMILES: CC(=N)N1CC[C@H](Oc2ccc([C@H](Cc3ccc4ccc(C(=N)N)cc4c3)C(=O)O)cc2)C1] | (S)-3-(7-carbamimidoylnaphthalen-2-yl)-2-(4-((S)-1-(1-iminoethyl)pyrrolidin-3-yloxy)phenyl)propanoic acid | as described in, e.g., Herbert, J. M., et al, J Pharmacol Exp Ther. 1996 276(3): 1030-8 |
| 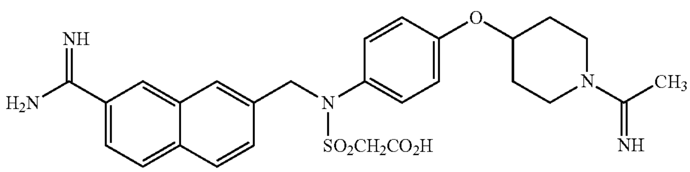 | 2-(N-((7-carbamimidoylnaphthalen-2-yl)methyl)-N-(4-(1-(1-iminoethyl)piperidin-4-yloxy)phenyl)sulfamoyl)acetic acid | as described in, e.g., Taniuchi, Y., et al, Thromb Haemost. 1998 79(3): 543-8 |
| 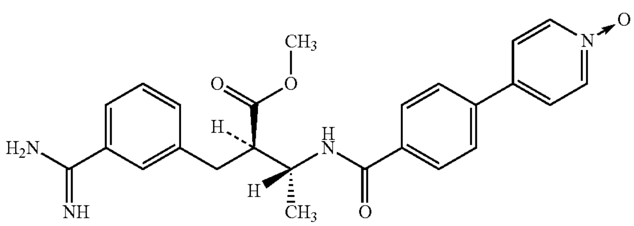 [SMILES: COC(=O)[C@H](Cc1cccc(C(=N)N)c1)[C@@H](C)NC(=O)c1ccc(-c2cc[n+]([O-])cc2)cc1] | methyl (2R,3R)-2-(3-carbamimidoylbenzyl)-3-[[4-(1-oxidopyridin-4-yl)benzoyl]amino]butanoate | Otamixaban |

The term "[2-({4-[(dimethylamino)iminomethyl]phenyl}carbonylamino)-5-methoxyphenyl]-N-(5-chloro(2-pyridyl))carboxamide," is intended to refer to the compound having the following structure or tautomers thereof, which is also referred to herein as betrixaban:

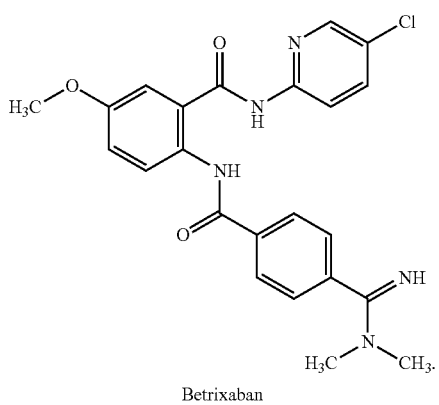 [SMILES: COc1ccc(NC(=O)c2ccc(C(=N)N(C)C)cc2)c(C(=O)Nc2ccc(Cl)cn2)c1]

Betrixaban

Betrixaban is described in U.S. Patent Application Publication US2007/0112039, which claims the benefit of U.S. Provisional Application Ser. No. 60/735,224 filed Nov. 8, 2005, the contents of which are incorporated herein by reference in their entirety. Betrixaban is known to be a specific inhibitor of factor Xa.

The term "factor XI inhibitors" or "inhibitors of factor XI" are compounds that can inhibit the coagulation factor XI. Upon proteolytic activation, factor XI is converted to the active enzyme factor XIa, which cleaves factor IX into factor IXa. Factor IXa then hydrolyzes factor X to factor Xa, which initiates the coagulation reactions that leads to blood clot formation as described above. An anti-factor XI antibody is a protein produced by an immune response that specifically binds factor XI, thus inhibits its activity. Some anti-factor XI antibodies are available commercially from, such as Haematologic Technologies, Essex Junction, Vt., USA.

"Injectable anticoagulants" are anticoagulant agents that are administrated to a mammal through injections. Examples of injectable anticoagulants are unfractionated heparin, low molecular weight heparins, and synthetic pentasaccharides.

"Antiplatelet agents" or "platelet inhibitors" are agents that block the formation of blood clots by preventing the aggregation of platelets. There are several classes of antiplatelet agents based on their activities, including, GP IIb/IIIa antagonists, such as abciximab (ReoPro®), eptifibatide (Integrilin®), and tirofiban (Aggrastat®); $P2Y_{12}$ receptor antagonists, such as clopidogrel (Plavix®), ticlopidine (Ticlid®), cangrelor, ticagrelor, and prasugrel; phosphodiesterase III (PDE III) inhibitors, such as cilostazol (Pletal®), dipyridamole (Persantine®) and Aggrenox® (aspirin/extended-release dipyridamole); thromboxane synthase inhibitors, such as furegrelate, ozagrel, ridogrel and isbogrel; thromboxane A2 receptor antagonists (TP antagonist), such as ifetroban, ramatroban, terbogrel, (3-{6-[(4-chlorophenylsulfonyl)amino]-2-methyl-5,6,7,8-tetrahydronaphth-1-yl}propionic acid (also known as Servier S 18886, by de Recherches Internationales Servier, Courbevoie, France); thrombin receptor antagonists, such as SCH530348 (having the chemical name of ethyl (1R,3aR,4aR,6R,8aR,9S,9aS)-9-((E)-2-(5-(3-fluorophenyl)pyridin-2-yl)vinyl)-1-methyl-3-oxododecahydronaphtho[2,3-] furan-6-ylcarbamate, by Schering Plough Corp., New Jersey, USA, described in US20040192753A1 and US2004/0176418A1 and studied in clinical trials, such as A Multicenter, Randomized, Double-Blind, Placebo-Controlled Study to Evaluate the Safety of SCH 530348 in Subjects Undergoing Non-Emergent Percutaneous Coronary Intervention with ClinicalTrials.gov Identifier: NCT00132912); P-selectin inhibitors, such as 2-(4-chlorobenzyl)-3-hydroxy-7,8,9,10-tetrahydrobenzo[H]quinoline-4-carboxylic acid (also known as PSI-697, by Wyeth, N.J., USA); and non-steroidal anti-inflammatory drugs (NSAIDS), such as acetylsalicylic acid (Aspirin®), resveratrol, ibuprofen (Advil®, Motrin®), naproxen (Aleve®, Naprosyn®), sulindac (Clinoril®), indomethacin (Indocin®), mefenamate, droxicam, diclofenac (Cataflam®, Voltaren®), sulfinpyrazone (Anturane®), and piroxicam (Feldene®). Among the NSAIDS, acetylsalicylic acid (ASA), resveratrol and piroxicam are preferred. Some NSAIDS inhibit both cyclooxygenase-1 (cox-1) and cyclooxygenase-2 (cox-2), such as aspirin and ibuprofen. Some selectively inhibit cox-1, such as resveratrol, which is a reversible cox-1 inhibitor that only weakly inhibits cox-2. Beta blockers and calcium channel blockers, which are described below, also have a platelet-inhibiting effect.

The term "pharmaceutically acceptable salts" is meant to include salts of the active compounds which are prepared with relatively nontoxic acids or bases, depending on the particular substituents found on the particular therapeutic agents described herein. When therapeutic agents described in the invention contain relatively acidic functionalities, base addition salts can be obtained by contacting the neutral form of such compounds with a sufficient amount of the desired base, either neat or in a suitable inert solvent. Examples of salts derived from pharmaceutically-acceptable inorganic bases include aluminum, ammonium, calcium, copper, ferric, ferrous, lithium, magnesium, manganic, manganous, potassium, sodium, zinc and the like. Salts derived from pharmaceutically-acceptable organic bases include salts of primary, secondary and tertiary amines, including substituted amines, cyclic amines, naturally-occurring amines and the like, such as arginine, betaine, caffeine, choline, N,N'-dibenzylethylenediamine, diethylamine, 2-diethylaminoethanol, 2-dimethylaminoethanol, ethanolamine, ethylenediamine, N-ethylmorpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine and the like. When therapeutic agents described in the invention contain relatively basic functionalities, acid addition salts can be obtained by contacting the neutral form of such compounds with a sufficient amount of the desired acid, either neat or in a suitable inert solvent. Examples of pharmaceutically acceptable acid addition salts include those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydriodic, or phosphorous acids and the like, as well as the salts derived from relatively nontoxic organic acids like acetic, propionic, isobutyric, malonic, benzoic, succinic, suberic, fumaric, mandelic, phthalic, benzenesulfonic, p-tolylsulfonic, citric, tartaric, methanesulfonic, and the like. Also included are salts of amino acids such as arginate and the like, and salts of organic acids like glucuronic or galactunoric acids and the like (see, e.g., Berge, S. M., et al, "Pharmaceutical Salts", Journal of Pharmaceutical Science, 1977, 66:1-19). Certain specific therapeutic agents contain both basic and acidic functionalities that allow the compounds to be converted into either base or acid addition salts.

Certain preferred salt forms for Compound A are described in U.S. Patent Application Publication US 2007/0123547, titled "[4-(6-Halo-7-substituted-2,4-dioxo-1,4-dihydro-2H-quinazolin-3-yl)-phenyl]-5-chloro-thiophen-2-yl-sulfonylureas And Forms And Methods Related Thereto," and filed Nov. 3, 2006, and claims priority from Provisional Application 60/733,650, filed on Nov. 3, 2005, both of which are hereby incorporated by reference in their entirety. Preferably, Compound A forms a potassium salt (Formula I):

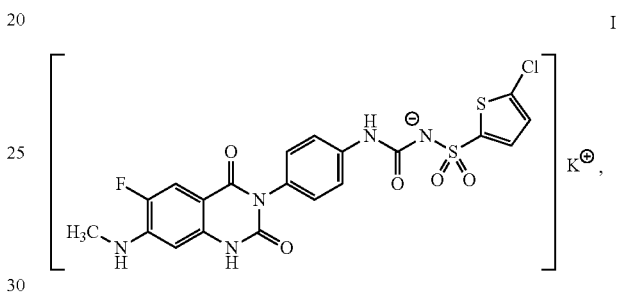

or a sodium salt (Formula II):

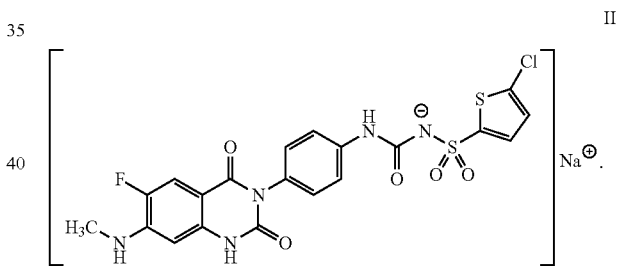

Several crystalline solid or amorphous forms of the potassium salt Formula I and sodium salt Formula II are also described in U.S. Patent Application Publication US 2007/0123547. Some preferred crystalline solid forms of the potassium salt Formula I have at least one of the following characteristics: (1) an infrared spectrum comprising peaks at about 3389 cm$^{-1}$ and about 1698 cm$^{-1}$; (2) an X-ray powder diffraction pattern comprising peaks at about 9.5 and about 25.5 °2θ; and (3) a DSC maximum endotherm at about 246° C. Among these forms, some have an infra red spectrum comprising absorption peaks at about 3559, 3389, 3324, 1698, 1623, 1563, 1510, 1448, 1431, 1403, 1383, 1308, 1269, 1206, 1174, 1123, 1091, 1072, 1030, 987, 939, 909, 871, 842, 787, 780, 769, 747, 718, 701, 690 and 667 cm$^{-1}$. Other preferred crystalline solid forms of the potassium salt Formula I have at least one of the following characteristics: (1) an infrared spectrum comprising peaks at about 3327 cm$^{-1}$ and about 1630 cm$^{-1}$; (2) an X-ray powder diffraction pattern comprising peaks at about 20.3 and about 25.1 °2θ; and (3) a DSC maximum endotherm at about 293° C. Among these forms, some have an infra red spectrum comprising absorption peaks at about 3584, 3327, 3189, 2935, 2257, 2067, 1979, 1903, 1703, 1654, 1630, 1590, 1557, 1512, 1444, 1429, 1406, 1375, 1317, 1346, 1317, 1288, 1276, 1243, 1217, 1182, 1133, 1182, 1133, 1093, 1072, 1033, 987, 943, 907, 883, 845, 831, 805, 776, 727, 694 and 674 $cm^{-1}$. Some preferred amorphous forms of the sodium salt Formula II have at least one of the following characteristics: (1) an infrared spectrum comprising peaks at about 3360, 1711, 1632, 1512, 1227, 1133 and 770 $cm^{-1}$; and (2) an X-ray powder diffraction pattern comprising a broad peak substantially between about 15 and about 30 °2θ. Among these forms, some have an infra red spectrum comprising absorption peaks at about 3360, 1711, 1632, 1556, 1512, 1445, 1407, 1375, 1309, 1280, 1227, 1133, 1092, 1032, 987, 905, 781, 770 and 691 $cm^{-1}$.

Certain preferred salt forms for betrixaban are disclosed in U.S. Patent Application Publication US2007/0112039. In particular, the application discloses that betrixaban forms a salt with an acid. The acid is preferably selected from the group consisting of hydrochloric, lactic, maleic, phenoxyacetic, propionic, succinic, adipic, ascorbic, camphoric, gluconic, phosphic, tartaric, citric, methanesulfonic, fumaric, glycolic, naphthalene-1,5-disulfonic, gentisic and benzenesulfonic. Preferably the acid is selected from the group consisting of hydrochloric, lactic, maleic, phenoxyacetic, propionic, and succinic. Most preferably, the acid is maleic acid, forming the maleate salt of betrixaban. One embodiment of the maleate salt of betrixaban exists as Formula III

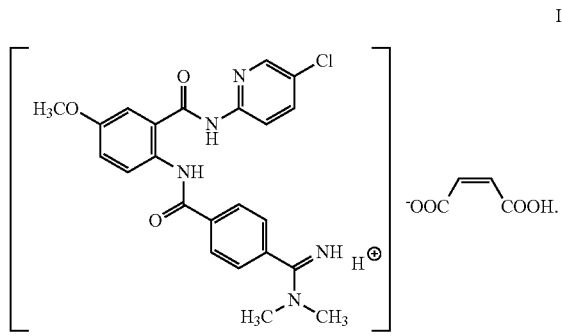

III

Further the salt of Formula III may exist in a crystalline polymorph as disclosed in U.S. Patent Application Publication US2007/0112039. One crystalline polymorph form of Formula III exhibits a powder X-ray diffraction pattern having at least four and preferably eight of the following approximate characteristic peak locations: 4.9, 9.7, 13.8, 14.1, 15.2, 17.6, 18.5, 20.8, 21.6, 22.7, 24.1, 26.3, 26.8 degrees 2θ. In a more preferred crystalline polymorph form, the powder X-ray diffraction pattern has approximate characteristic peak locations of 4.9, 9.7, 11.8, 13.8, 14.1, 15.2, 17.6, 18.5, 19.9, 20.8, 21.6, 22.7, 24.1, 25.0, 26.3, 26.8 degrees 2θ.

The neutral forms of the therapeutic agents may be regenerated by contacting the salt with a base or acid and isolating the parent therapeutic agent in the conventional manner. The parent form of the therapeutic agent differs from the various salt forms in certain physical properties, such as solubility in polar solvents, but otherwise the salts are equivalent to the parent form for the purposes of the present invention.

In addition to salt forms, certain therapeutic agents are in a prodrug form. Prodrugs of the therapeutic agents are those compounds that readily undergo chemical changes under physiological conditions to provide the compound having therapeutic activities. Additionally, prodrugs can be converted to the active compound by chemical or biochemical methods in an ex vivo environment. For example, prodrugs can be slowly converted to the active compound described in the invention when placed in a transdermal patch reservoir with a suitable enzyme or chemical reagent.

Certain therapeutic agents described in the invention can exist in unsolvated forms as well as solvated forms, including hydrated forms. In general, the solvated forms are equivalent to unsolvated forms and are intended to be encompassed within the scope of the present invention. Certain therapeutic agents may exist in multiple crystalline or amorphous forms. In general, all physical forms are equivalent for the uses contemplated by the present invention and are intended to be within the scope of the present invention.

"Pharmaceutically acceptable carriers" refer to any diluents, excipients, or carriers that may be used in the compositions of the invention. Pharmaceutically acceptable carriers include ion exchangers, alumina, aluminum stearate, lecithin, serum proteins, such as human serum albumin, buffer substances, such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat. Suitable pharmaceutical carriers are described in *Remington's Pharmaceutical Sciences*, Mack Publishing Company, a standard reference text in this field. They are preferably selected with respect to the intended form of administration, that is, oral tablets, capsules, elixirs, syrups and the like, and consistent with conventional pharmaceutical practices.

II. Detailed Description of the Embodiments a. Methods of Treatment

The present invention provides novel methods for treating a condition in a mammal characterized by undesired thrombosis comprising administering to said mammal a therapeutically effective amount of the following therapeutic agents:

(1) [4-(6-fluoro-7-methylamino-2,4-dioxo-1,4-dihydro-2H-quinazolin-3-yl)-phenyl]-5-chloro-thiophen-2-yl-sulfonylurea, or a pharmaceutically acceptable salt thereof; and (2) a second therapeutic agent selected from the group consisting of an anticoagulant, an antiplatelet agent, or combinations thereof.

In one aspect, the invention provides a novel method for preventing or treating thrombosis and/or a thrombosis-related condition in a mammal comprising administering to said mammal a therapeutically effective amount of the following two therapeutic agents:

(1) [4-(6-fluoro-7-methylamino-2,4-dioxo-1,4-dihydro-2H-quinazolin-3-yl)-phenyl]-5-chloro-thiophen-2-yl-sulfonylurea, or a pharmaceutically acceptable salt thereof; and (2) an anticoagulant agent.

In some embodiments, the anticoagulant agent is an inhibitor of factor Xa. In some embodiments, the factor Xa inhibitor is a specific factor Xa inhibitor.

In some embodiments, the factor Xa inhibitor is YM-150, Daiichi DU-176b, LY517717, or a compound selected from Table 1.

In some embodiments, the factor Xa inhibitor is rivaroxaban.

In some embodiments, the specific inhibitor of factor Xa is betrixaban, or a pharmaceutically acceptable salt thereof. In still some embodiments, the pharmaceutically acceptable salt of betrixaban is the maleate salt.

In other embodiments, the anticoagulant agent is selected from the group consisting of specific inhibitors of thrombin, factor IXa, factor XI, factor XIa or factor VIIa. In some embodiments, the anticoagulant agent is selected from the group consisting of bivalirudin, argatroban, lepirudin, warfarin, ximelagatran, AZD0837, RB2006, dabigatran and phenocoumarol.

In still other embodiments, the anticoagulant agent is an injectable anticoagulant agent. In some embodiments, the anticoagulant agent is selected from the group consisting of synthetic pentasaccharides and low molecular weight heparin. In some embodiments, the anticoagulant agent is selected from the group consisting of fondaparinux, danaparoid, enoxaparin, dalteparin and unfractionated heparin.

In other embodiments, the anticoagulant agent is an anti-factor XI antibody. In still other embodiments, the anticoagulant agent is bivalirudin.

In another aspect, the invention provides a method for treating a condition in a mammal characterized by undesired thrombosis in a mammal comprising administering to said mammal a therapeutically effective amount of the following two therapeutic agents:
  (1) [4-(6-fluoro-7-methylamino-2,4-dioxo-1,4-dihydro-2H-quinazolin-3-yl)-phenyl]-5-chloro-thiophen-2-yl-sulfonylurea, or a pharmaceutically acceptable salt thereof; and
  (2) another antiplatelet agent.

In some embodiments, the antiplatelet agent is an antagonist of the TP receptor. In some embodiments, the antagonist of the TP receptor is ifetroban. In other embodiments, the antiplatelet agent is a cyclooxygenase inhibitor. In some embodiments, the cyclooxygenase inhibitor is acetylsalicylic acid. In some embodiments, the antiplatelet agent is a reversible cyclooxygenase-1 inhibitor. In some embodiments, the reversible cyclooxygenase-1 inhibitor is resveratrol.

In some embodiments, the other antiplatelet agent is selected from the group consisting of abciximab, eptifibatide, tirofiban, dipyridamole, aggrenox, cilostazol, isbogrel, furegrelate and ozagrel.

In some embodiments, at least one of the therapeutic agents is administered in a sub-therapeutic dosage.

In some embodiments, both of the therapeutic agents are administered in sub-therapeutic dosages.

In some embodiments, the two therapeutic agents are administered simultaneously.

In some embodiments, the two therapeutic agents are administered sequentially.

In still another aspect, the invention provides a method for preventing or treating thrombosis and/or a thrombosis-related condition in a mammal comprising administering to said mammal a therapeutically effective amount of the following three therapeutic agents:
  (1) [4-(6-fluoro-7-methylamino-2,4-dioxo-1,4-dihydro-2H-quinazolin-3-yl)-phenyl]-5-chloro-thiophen-2-yl-sulfonylurea, or a pharmaceutically acceptable salt thereof;
  (2) another antiplatelet agent; and
  (3) an anticoagulant agent.

In some embodiments, the antiplatelet agent is a cyclooxygenase inhibitor. In some embodiments, the antiplatelet agent is acetylsalicylic acid. In other embodiments, the antiplatelet agent is an antagonist of TP receptor. In some embodiments, it is ifetroban. In some embodiments, the anticoagulant agent is a factor Xa inhibitor. In some embodiments, it is betrixaban.

In some embodiments, at least one of the therapeutic agents is administered in a sub-therapeutic dosage. In some embodiments, all of the therapeutic agents are administered in sub-therapeutic dosages.

In some embodiments, the three therapeutic agents are administered simultaneously. In some embodiments, the three therapeutic agents are administered sequentially.

In some embodiments, the pharmaceutically acceptable salt of [4-(6-fluoro-7-methylamino-2,4-dioxo-1,4-dihydro-2H-quinazolin-3-yl)-phenyl]-5-chloro-thiophen-2-yl-sulfonylurea is the potassium salt.

In some embodiments, the pharmaceutically acceptable salt of [4-(6-fluoro-7-methylamino-2,4-dioxo-1,4-dihydro-2H-quinazolin-3-yl)-phenyl]-5-chloro-thiophen-2-yl-sulfonylurea is the sodium salt.

In some embodiments, the thrombosis-related condition is selected from the group consisting of acute myocardial infarction, unstable angina, chronic stable angina, transient ischemic attacks, strokes, peripheral vascular disease, preeclampsia/eclampsia, deep venous thrombosis, embolism, disseminated intravascular coagulation and thrombotic cytopenic purpura, thrombotic and restenotic complications following invasive procedures resulting from angioplasty, carotid endarterectomy, post CABG (Coronary artery bypass graft) surgery, vascular graft surgery, stent placements and insertion of endovascular devices and prosthesis.

b. Pharmaceutical Compositions

This invention also provides pharmaceutical compositions comprising a pharmaceutically acceptable carrier, [4-(6-fluoro-7-methylamino-2,4-dioxo-1,4-dihydro-2H-quinazolin-3-yl)-phenyl]-5-chloro-thiophen-2-yl-sulfonylurea, or a pharmaceutically acceptable salt thereof and at least another therapeutic agent selected from the group consisting of an anticoagulant agent, an antiplatelet agent, and combinations thereof.

In one aspect, the invention provides a pharmaceutical composition comprising the following two therapeutic agents:
  (1) [4-(6-fluoro-7-methylamino-2,4-dioxo-1,4-dihydro-2H-quinazolin-3-yl)-phenyl]-5-chloro-thiophen-2-yl-sulfonylurea, or a pharmaceutically acceptable salt thereof; and
  (2) an anticoagulant agent;
  and a pharmaceutically acceptable carrier.

In some embodiments, the anticoagulant agent is an inhibitor of factor Xa.

In some embodiments, the factor Xa inhibitor is a specific factor Xa inhibitor.

In some embodiments, the factor Xa inhibitor is YM-150, Daiichi DU-176b, LY517717, or a compound selected from Table 1.

In some embodiments, the factor Xa inhibitor is rivaroxaban.

In some embodiments, the specific inhibitor of factor Xa is betrixaban, or a pharmaceutically acceptable salt thereof. In still some embodiments, the pharmaceutically acceptable salt of betrixaban is the maleate salt.

In other embodiments, the anticoagulant is selected from the group consisting of specific inhibitors of thrombin, factor IXa, factor XI, factor XIa or factor VIIa. In some embodiments, the anticoagulant agent is selected from the group consisting of bivalirudin, argatroban, lepirudin, warfarin, and phenocoumarol.

In other embodiments, the anticoagulant agent is an injectable anticoagulant agent.

In some embodiments, the anticoagulant agent is selected from the group consisting of synthetic pentasaccharides, and low molecular weight heparin.

In some embodiments, the anticoagulant agent is selected from the group consisting of fondaparinux, danaparoid, enoxaparin, dalteparin and unfractionated heparin.

In other embodiments, the anticoagulant agent is an inhibitor of factor XI. In some embodiments, the inhibitor of factor XI is an anti-factor XI antibody.

In still other embodiments, the anticoagulant agent is bivalirudin.

In still some embodiments, the anticoagulant is ximelagatran, AZD0837 or dabigatran.

In another aspect, the invention provides a pharmaceutical composition comprising the following two therapeutic agents:
  (1) [4-(6-fluoro-7-methylamino-2,4-dioxo-1,4-dihydro-2H-quinazolin-3-yl)-phenyl]-5-chloro-thiophen-2-yl-sulfonylurea, or a pharmaceutically acceptable salt thereof; and
  (2) another antiplatelet agent;
  and a pharmaceutically acceptable carrier.

In some embodiments, the antiplatelet agent is an antagonist of TP receptor. In some embodiments, the antagonist of TP receptor is ifetroban.

In other embodiments, the antiplatelet agent is a cyclooxygenase inhibitor. In some embodiments, the cyclooxygenase inhibitor is acetylsalicylic acid. In some embodiments, the antiplatelet agent is a reversible cyclooxygenase-1 inhibitor. In some embodiments, the reversible cyclooxygenase-1 inhibitor is resveratrol.

In some embodiments, the antiplatelet agent is selected from the group consisting of abciximab, eptifibatide, tirofiban, dipyridamole, aggrenox, cilostazol, isbogrel, furegrelate and ozagrel.

In still another aspect, the invention provides a pharmaceutical composition comprising a pharmaceutically acceptable carrier and the following three therapeutic agents:
  (1) [4-(6-fluoro-7-methylamino-2,4-dioxo-1,4-dihydro-2H-quinazolin-3-yl)-phenyl]-5-chloro-thiophen-2-yl-sulfonylurea, or a pharmaceutically acceptable salt thereof;
  (2) another antiplatelet agent; and
  (3) an anticoagulant agent.

In some embodiments, the antiplatelet agent is a cyclooxygenase inhibitor. In some embodiments, the antiplatelet agent is acetylsalicylic acid. In other embodiments, the antiplatelet agent is an antagonist of TP receptor. In some embodiments, it is ifetroban. In some embodiments, the anticoagulant agent is a factor Xa inhibitor. In some embodiments, it is betrixaban.

In some embodiments, at least one of the therapeutic agents is present in a sub-therapeutic dosage.

In some embodiments, all of the therapeutic agents are present in sub-therapeutic dosages.

In some embodiments, the pharmaceutically acceptable salt of [4-(6-fluoro-7-methylamino-2,4-dioxo-1,4-dihydro-2H-quinazolin-3-yl)-phenyl]-5-chloro-thiophen-2-yl-sulfonylurea is the potassium salt.

In some embodiments, the pharmaceutically acceptable salt of [4-(6-fluoro-7-methylamino-2,4-dioxo-1,4-dihydro-2H-quinazolin-3-yl)-phenyl]-5-chloro-thiophen-2-yl-sulfonylurea is the sodium salt.

c. Kit

This invention also provides novel kits comprising
  (1) a first container, wherein said first container contains [4-(6-fluoro-7-methylamino-2,4-dihydro-2H-quinazolin-3-yl)-phenyl]-5-chloro-thiophen-2-yl-sulfonylurea, or a pharmaceutically acceptable salt thereof; and
  (2) a second container, wherein said second container contains a second therapeutic agent selected from the group consisting of an anticoagulant agent, an antiplatelet agent, and a combination thereof.

In one aspect, the invention provides a kit comprising:
  (1) a first container, wherein said first container contains [4-(6-fluoro-7-methylamino-2,4-dioxo-1,4-dihydro-2H-quinazolin-3-yl)-phenyl]-5-chloro-thiophen-2-yl-sulfonylurea, or a pharmaceutically acceptable salt thereof; and
  (2) a second container, wherein said second container contains an anticoagulant agent.

In still another aspect, the invention provides a kit comprising:
  (1) a first container, wherein said first container contains [4-(6-fluoro-7-methylamino-2,4-dioxo-1,4-dihydro-2H-quinazolin-3-yl)-phenyl]-5-chloro-thiophen-2-yl-sulfonylurea, or a pharmaceutically acceptable salt thereof; and
  (2) a second container, wherein said second container contains an another antiplatelet agent.

In some embodiments, at least one of the therapeutic agents is present in a sub-therapeutic dosage.

In some embodiments, both of the therapeutic agents are present in sub-therapeutic dosages.

In some embodiments, the kit further comprises a package insert stating that the two therapeutic agents can be used together.

In still another aspect, the invention provides a kit comprising:
  (1) a first container, wherein said first container contains [4-(6-fluoro-7-methylamino-2,4-dioxo-1,4-dihydro-2H-quinazolin-3-yl)-phenyl]-5-chloro-thiophen-2-yl-sulfonylurea, or a pharmaceutically acceptable salt thereof;
  (2) a second container, wherein said second container contains an anticoagulant agent; and
  (3) a third container, wherein said third container contains an another antiplatelet agent.

In some embodiments, the first container contains [4-(6-fluoro-7-methylamino-2,4-dioxo-1,4-dihydro-2H-quinazolin-3-yl)-phenyl]-5-chloro-thiophen-2-yl-sulfonylurea potassium salt.

In some embodiments, the first container contains [4-(6-fluoro-7-methylamino-2,4-dioxo-1,4-dihydro-2H-quinazolin-3-yl)-phenyl]-5-chloro-thiophen-2-yl-sulfonylurea sodium salt.

In some embodiments, the second container contains betrixaban, or a pharmaceutically acceptable salt thereof.

In still some embodiments, the second container contains betrixaban maleate salt.

III. Combination Therapy

It is contemplated that a combination of Compound A with a factor Xa inhibitor, such as betrixaban, will produce additional antithrombotic effect over the two agents alone. Example 3 shows that addition of varying concentrations of betrixaban to 1.1 µM of Compound A provided additional thrombosis inhibition in a dose responsive manner in a perfusion chamber assay. Similarly, as shown by Example 4, addition of varying amount of Compound A to a fixed amount of betrixaban also produced additional inhibition of thrombosis formation in a dose responsive manner. Similar additive results were obtained in a platelet-initiated thrombin generation assay as shown in Example 5, where the combination of Compound A and betrixaban provided greater inhibition than either compound alone.

Inhibitors of other coagulation enzymes, such as factor XI inhibitors or direct thrombin inhibitors, may also be combined with Compound A to achieve improved antithrombotic efficacy. Example 6 illustrates that the combination of an antibody of factor XI with Compound A was capable of inhibiting thrombus formation in assay conditions where neither Compound A nor the factor XI antibody alone was able to produce detectable inhibition of thrombus formation. Example 7 illustrates that combination of Compound A with a factor XI antibody produced more inhibition of thrombus formation than Compound A alone or a combination of Compound A and betrixaban in a perfusion assay. Example 8 illustrates the combined antithrombotic effect observed when Compound A is combined with a direct thrombin inhibitor, such as bivalirudin (Angiomax®).

Not only can Compound A provide additive antithrombotic benefit with an anticoagulant agent, it is also contemplated that Compound A, an antiplatelet agent acting through $P2Y_{12}$ antagonism, can be combined with other classes of antiplatelet agents to produce additional antithrombotic benefit. As shown in Examples 9 and 10, additional antithrombotic benefit was obtained when Compound A was combined with either a cyclooxygenase inhibitor, such as acetylsalicylic acid (Example 9), or a TP antagonist, such as ifetroban (Example 10), in the presence of a factor Xa inhibitor.

It is contemplated that the method of treatment using a combination of Compound A and a co-administered agent will not produce undesired drug-drug interaction or other additional side effects over the agents alone. Preferably, the combination can offer an improved efficacy and/or safety advantage over the agents alone, particularly when smaller dosing is required to achieve a theraprutic result. In such a case, the therapeutically effective amount of the agents in the combination therapy may be lower than the effective or optimal amount needed when the agents are used alone. It is contemplated that lower dosages will minimize potential side effects of an agent, thus lead to improved safety profile. Thus, the combination preferably allows one of the therapeutic agents to be used at a sub-therapeutic dosage. Still more preferably, the combination allows both therapeutic agents to be used at sub-therapeutic dosages.

Similarly, it is contemplated that the method of treatment using a combination of Compound A, an anticoagulant agent and another antiplatelet agent will not produce undesired drug-drug interaction or other additional side effects over use of any of the agents alone. Preferably the combination of three agents can offer an efficacy or safety advantage over the use of any of the agents alone. More preferably the combination allows one of the therapeutic agents be used at lower doses than that is required when the therapeutic agent is used alone, i.e. at sub-therapeutic dosages. Still more preferably, the combination allows all therapeutic agents to be used at sub-therapeutic dosages.

Compound A and the co-administered agent may be formulated into two separate pharmaceutical compositions. They may be administered at the same time or sequentially in any order. Preferably, when administered sequentially, the two agents are administered sufficiently closely in time so that the desired therapeutic effect can be provided. Compound A and the co-administered agent may also be formulated into a single pharmaceutical composition. Compound A, an anticoagulant agent and another antiplatelet agent may also be administered at the same time or sequentially in any order. Preferably, when administered sequentially, the three agents are administered sufficiently closely in time so that the desired therapeutic effect can be provided. They may also be formulated into a single pharmaceutical composition or any two of them may be formulated into a single pharmaceutical composition.

Any of the above dosage forms containing effective amounts are within the bounds of routine experimentation and within the scope of the invention. A therapeutically effective dose may vary depending upon the route of administration and dosage form. The preferred combination of the invention is a formulation that exhibits a high therapeutic index. The therapeutic index is the dose ratio between toxic and therapeutic effects which can be expressed as the ratio between $LD_{50}$ and $ED_{50}$. The $LD_{50}$ is the dose lethal to 50% of the population and the $ED_{50}$ is the dose therapeutically effective in 50% of the population. The $LD_{50}$ and $ED_{50}$ are determined by standard pharmaceutical procedures in animal cell cultures or experimental animals. Combination therapies of this invention may be administered once or several times daily and other dosage regimens may also be useful. Preferably, combination therapies of this invention are administered in a single daily dose, or administered two, three, or four times daily. More preferably, combination therapies of this invention are administered once or twice daily.

Typically, about 0.5 to 500 mg of Compound A, or a salt or mixture of salts of Compound A is compounded with a physiologically acceptable vehicle, carrier, excipient, binder, preservative, stabilizer, dye, flavor etc., as called for by accepted pharmaceutical practice. In one aspect, Compound A is formulated into a formulation suitable for intravenous administration. In some embodiments, a unit dose of the intravenous formulation contains from 1 to 50 mg of Compound A or a pharmaceutically acceptable salt. In other embodiments, the unit dose contains from 5 to 40 mg, 10 to 30 mg, 15 to 25 mg, 25 to 45 mg, or about 20 mg, 30, 40, or 50 mg of Compound A or the salt.

In another aspect, Compound A is formulated into a formulation suitable for oral administration. In some embodiments, the composition is formulated as a unit dose containing from 1 to 800 mg, 20 to 200 mg, 50 to 150 mg, 10 to 50 mg, or 20 to 40 mg of Compound A or a salt. In some embodiments, the composition is in a unit dose format and contains about 30, 50, 75, 100, 125, 150, 175, or 200 mg of Compound A or a salt.

When Compound A and the co-administered agent are formulated into a single pharmaceutical composition, about 0.5 to 500 mg of the co-administered agent can be added to the above composition. Preferably, when Compound A and the other agent are formulated in an intravenous formulation, Compound A or a salt thereof is present in the amount of 1 to 50 mg, 5 to 40 mg, 10 to 30 mg, 15 to 25 mg, 25 to 45 mg, or about 20 mg, 30, 40, or 50 mg. When Compound A and the other agent are formulated in an oral formulation, Compound A or a salt is present in the amount of from 1 to 800 mg, 20 to 200 mg, 50 to 150 mg, 10 to 50 mg, or 20 to 40 mg or about 30, 50, 75, 100, 125, 150, 175, or 200 mg. In combinations containing Compound A and betrixaban, any of the above unit doses of Compound A or a salt or mixture of salts of Compound A and about 0.5 to 500 mg of betrixaban or a salt or mixture of salts of betrixaban are compounded with a physiologically acceptable vehicle, carrier, excipient, binder, preservative, stabilizer, dye, flavor etc., as called for by accepted pharmaceutical practice. The amount of active ingredient(s) in these compositions is such that a suitable dosage in the range indicated is obtained.

It is contemplated that a typical dosage of Compound A in the combination therapies will range from about 0.001 mg/kg to about 100 mg/kg, preferably about 0.01 mg/kg to about 11.4 mg/kg, more preferably from about 0.01 mg/kg to about 2.85 mg/kg, and even more preferably from about 0.01 mg/kg to about 1.43 mg/kg. In combination therapies containing Compound A and betrixaban, it is contemplated that a typical dosage of betrixaban will range from about 0.001 mg/kg to about 1000 mg/kg, preferably from about 0.01 mg/kg to about 2.0 mg/kg, and more preferably from about 0.1 mg/kg to about 1.5 mg/kg, or from about 0.4 mg/kg to about 1.2 mg/kg, and even more preferably from about 0.5 mg/kg to about 1.0 mg/kg. Still more preferably, the dosage of betrixaban in the combinations is lower than 0.5 mg/kg.

The typical dosages of the other co-administered agents described herein when used as a single agent are known to a person skilled in the art. It is contemplated that the dosages of these agents when used in combination with Compound A will not exceed the maximum dosages of the individual agents. Preferably, the dosages in the combination therapies are less than the maximum dosages and more preferably, the dosages in the combination therapies are sub-therapeutic dosages. It is contemplated that the dosages can be adjusted to reflect the improved benefit achieved by the combination therapies, which can be determined by one skilled in the art based on the information given herein.

IV. Composition

The present invention further provides a novel composition comprising Compound A or a pharmaceutically acceptable salt thereof, an anticoagulant agent or another antiplatelet agent, and a pharmaceutically acceptable carrier.

The pharmaceutical compositions of the invention can be manufactured by methods well known in the art such as conventional granulating, mixing, dissolving, encapsulating, lyophilizing, or emulsifying processes, among others. Compositions may be produced in various forms, including granules, precipitates, or particulates, powders, including freeze dried, rotary dried or spray dried powders, amorphous powders, tablets, capsules, syrup, suppositories, injections, emulsions, elixirs, suspensions or solutions. Formulations may optionally contain stabilizers, pH modifiers, surfactants, bioavailability modifiers and combinations of these.

Pharmaceutical formulations may be prepared as liquid suspensions or solutions using a sterile liquid, such as oil, water, alcohol, and combinations thereof. Pharmaceutically suitable surfactants, suspending agents or emulsifying agents, may be added for oral or parenteral administration. Suspensions may include oils, such as peanut oil, sesame oil, cottonseed oil, corn oil and olive oil. Suspension preparation may also contain esters of fatty acids, such as ethyl oleate, isopropyl myristate, fatty acid glycerides and acetylated fatty acid glycerides. Suspension formulations may include alcohols, such as ethanol, isopropyl alcohol, hexadecyl alcohol, glycerol and propylene glycol. Ethers, such as poly(ethyleneglycol), petroleum hydrocarbons, such as mineral oil and petrolatum, and water may also be used in suspension formulations.

The compositions of this invention are formulated for pharmaceutical administration to a mammal, preferably a human being. Such pharmaceutical compositions of the invention may be administered orally, parenterally, by inhalation spray, topically, rectally, nasally, buccally, vaginally or via an implanted reservoir. The term "parenteral" as used herein includes subcutaneous, intravenous, intramuscular, intra-articular, intra-synovial, intrasternal, intrathecal, intrahepatic, intralesional and intracranial injection or infusion techniques. Preferably, the compositions are administered orally or intravenously. The formulations of the invention may be designed as short-acting, fast-releasing, long-acting, sustained-releasing. Still further, compounds can be administered in a local rather than systemic means, such as administration (e.g., injection) as a sustained release formulation.

Sterile injectable forms of the compositions of this invention may be aqueous or oleaginous suspension. These suspensions may be formulated according to techniques known in the art using suitable dispersing or wetting agents and suspending agents. The sterile injectable preparation may also be a sterile injectable solution or suspension in a non-toxic parenterally acceptable diluent or solvent, for example as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium. For this purpose, any bland fixed oil may be employed including synthetic mono- or di-glycerides. Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions may also contain a long-chain alcohol diluent or dispersant, such as carboxymethyl cellulose or similar dispersing agents which are commonly used in the formulation of pharmaceutically acceptable dosage forms including emulsions and suspensions. Other commonly used surfactants, such as Tweens, Spans and other emulsifying agents or bioavailability enhancers which are commonly used in the manufacture of pharmaceutically acceptable solid, liquid, or other dosage forms may also be used for the purposes of formulation. Compounds may be formulated for parenteral administration by injection such as by bolus injection or continuous infusion. A unit dosage form for injection may be in ampoules or in multi-dose containers.

The pharmaceutical compositions of this invention may be in any orally acceptable dosage form, including capsules, tablets, aqueous suspensions or solutions. In the case of tablets for oral use, carriers that are commonly used include lactose and corn starch. Lubricating agents, such as magnesium stearate, are also typically added. For a capsule form, useful diluents include lactose and dried cornstarch. When aqueous suspensions are required for oral use, the active ingredient is combined with emulsifying and suspending agents. If desired, certain sweetening, flavoring or coloring agents may also be added.

Alternatively, the pharmaceutical compositions of this invention may be in the form of suppositories for rectal administration. These may be prepared by mixing the agent with a suitable non-irritating excipient which is solid at room temperature but liquid at rectal temperature and therefore will melt in the rectum to release the drug. Such materials include cocoa butter, beeswax and polyethylene glycols.

The pharmaceutical compositions of this invention may also be in a topical form, especially when the target of treatment includes areas or organs readily accessible by topical application, including diseases of the eye, the skin, or the lower intestinal tract. Suitable topical formulations are readily prepared for each of these areas or organs.

Topical application for the lower intestinal tract may be effected in a rectal suppository formulation (see above) or in a suitable enema formulation. Topically-transdermal patches may also be used. For topical applications, the pharmaceutical compositions may be formulated in a suitable ointment containing the active component suspended or dissolved in one or more carriers. Carriers for topical administration of the compounds of this invention include, but are not limited to, mineral oil, liquid petrolatum, white petrolatum, propylene glycol, polyoxyethylene, polyoxypropylene compound, emulsifying wax and water. Alternatively, the pharmaceutical compositions may be formulated in a suitable lotion or cream containing the active components suspended or dissolved in one or more pharmaceutically acceptable carriers. Suitable carriers include mineral oil, sorbitan monostearate, polysorbate 60, cetyl esters, wax, cetyl alcohol, 2-octyldodecanol, benzyl alcohol and water.

For ophthalmic use, the pharmaceutical compositions may be formulated as micronized suspensions in isotonic, pH adjusted sterile saline, or, preferably, as solutions in isotonic, pH adjusted sterile saline, either with our without a preservative, such as benzylalkonium chloride. Alternatively, for ophthalmic uses, the pharmaceutical compositions may be formulated in an ointment, such as petrolatum.

The pharmaceutical compositions of this invention may also be administered by nasal aerosol or inhalation. Such compositions are prepared according to techniques known in the art of pharmaceutical formulation and may be prepared as solutions in saline, employing benzyl alcohol or other suitable preservatives, absorption promoters to enhance bioavailability, fluorocarbons and/or other conventional solubilizing or dispersing agents.

In addition to dosage forms described above, pharmaceutically acceptable excipients and carriers and dosage forms are generally known to those skilled in the art and are included in the invention. It should be understood that a specific dosage and treatment regimen for any particular patient will depend upon a variety of factors, including the activity of the specific compound employed, the age, body weight, general health, sex and diet, renal and hepatic function of the patient, and the time of administration, rate of excretion, drug combination, judgment of the treating physician or veterinarian and severity of the particular disease being treated. The amount of active ingredients will also depend upon the therapeutic agent combined with Compound A.

V. Kit of Parts

The invention further provides a novel kit or package. In some embodiments, the kit of the present invention comprises: (a) a first container containing Compound A or pharmaceutically acceptable salt forms thereof; and (b) a second container containing an anticoagulant agent or another antiplatelet agent. In other embodiments, the kit comprises: (a) a first container containing Compound A or pharmaceutically acceptable salt forms thereof; (b) a second container containing an anticoagulant agent and (c) a third container containing another antiplatelet agent. In some embodiments, the kit further contains a package insert stating that the two pharmaceutical agents can be used together for the treatment of a condition characterized by undesired thrombosis.

The first, second, or third container can be a bottle, jar, vial, flask, syringe, tube, bag, or any other container used in the manufacture, storage, or distribution of a pharmaceutical product. The package insert can be a label, tag, marker, or the like, that recites information relating to the pharmaceutical composition of the kit. The information recited will usually be determined by the regulatory agency governing the area in which the pharmaceutical composition is to be sold, such as the United States Food and Drug Administration. Preferably, the package insert specifically recites the indications for which the pharmaceutical composition has been approved. The package insert may be made of any material on which a person can read information contained therein or thereon. Preferably, the package insert is a printable material, such as paper, adhesive-backed paper cardboard, foil, or plastic, and the like, on which the desired information has been printed or applied.

VI. Examples

Unless stated otherwise, the abbreviations used throughout the specification have the following meanings:
ACN=acetonitrile
API=active pharmaceutical ingredient
aq.=aqueous
Boc=tert-butoxylcarbonyl
DCM=dichloromethane
DMSO=dimethyl sulfoxide
eq.=equivalent
EtOH=ethanol
g=gram
HPLC=high performance liquid chromatography
hr=hour
kg=kilogram
KOH=potassium hydroxide
L=liter
LOD=limit of detection
M=molar
Me=methyl
MeO=methoxy
MeOH=methanol
mg=milligram
min=minute
mL=milliliter
mm=millimeter
N=normal
ng=nanogram
nM=nanomolar
NMR=nuclear magnetic resonance
pg=picogram
pM=picomolar
psi pound per square inch
sec=second
THF=tetrahydrofuran
TLC=thin layer chromatography
WFI=water for injection
µM=micromolar
µg=microgram
Z-gly-gly-arg-AMC=carbobenzyloxy-glycine-glycine-arginine-4-aminomethylcoumarin
VC=vehicle control
NS=nonsignificant

Example 1

Preparation of Compound A and Its Potassium Salt
Formula I

Scheme 1

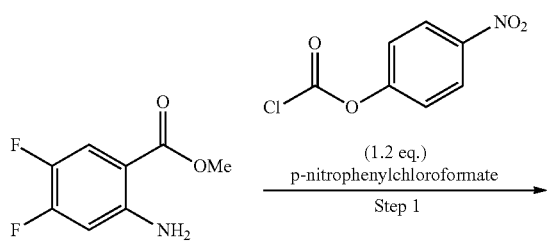

-continued
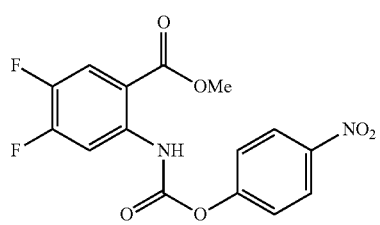
2
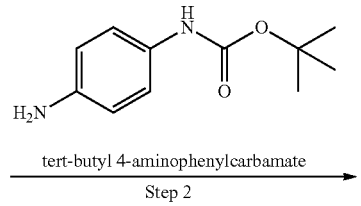
tert-butyl 4-aminophenylcarbamate
Step 2
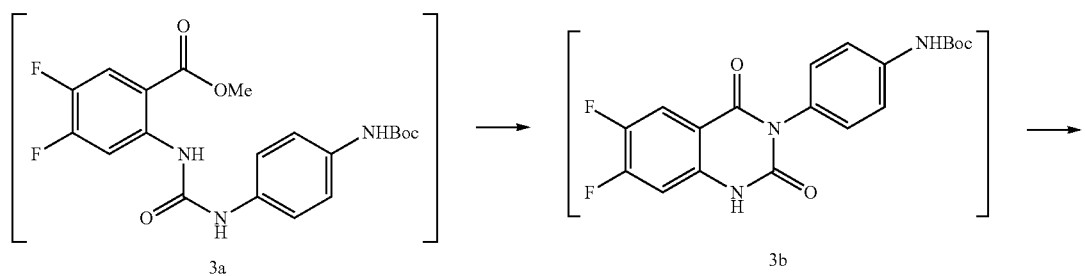
3a    3b
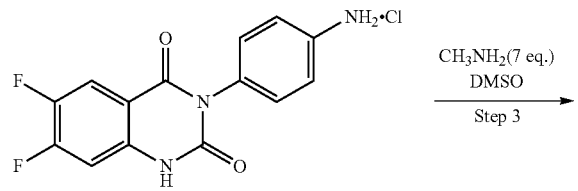
3
CH₃NH₂ (7 eq.)
DMSO
Step 3
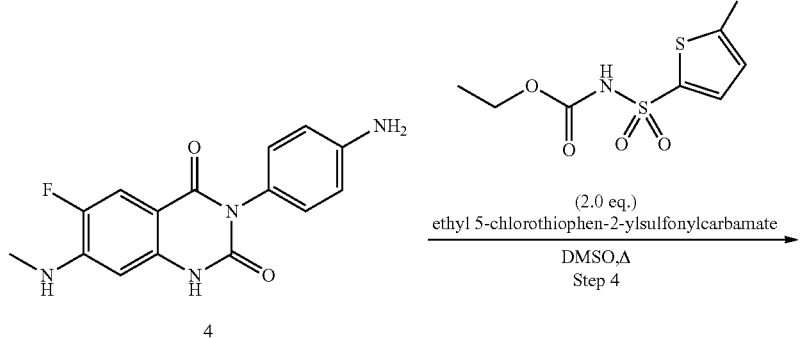
4
(2.0 eq.)
ethyl 5-chlorothiophen-2-ylsulfonylcarbamate
DMSO, Δ
Step 4
2 N KOH (1.15 eq.)
ACN/H₂O,
50° C., 1 h
Step 5
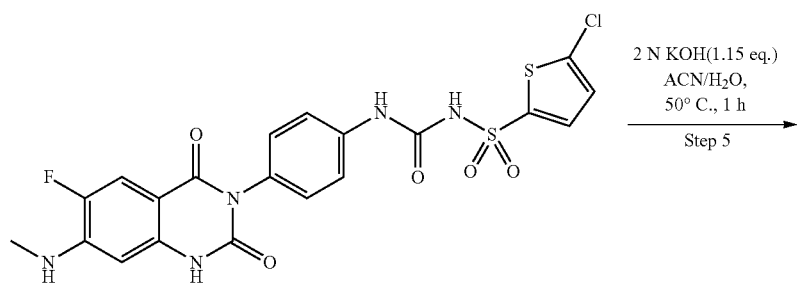
Compound A

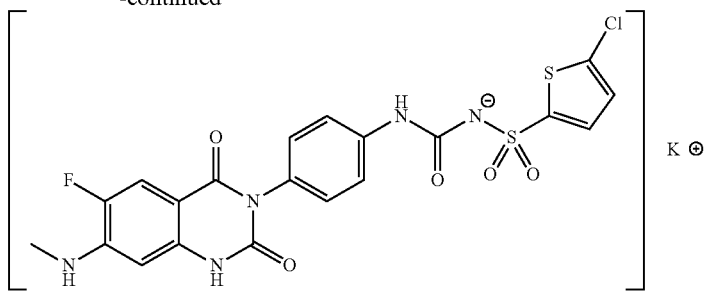

Formula I

Step 1:

Methyl 2-amino-4,5-difluorobenzoate (1) (38 kg, 1.0 eq.) and dichloromethane (560 kg, 8X, ACS>99.5%) were charged to a 2000 L GL reactor. The reaction mixture was agitated for 5 mins. 4-Nitrophenylchloroformate (49.1 kg, 1.2 eq.) was charged into the 200 L reactor followed by dichloromethane (185 kg) and the contents were agitated for 5 mins. After pressurizing the 200 L reactor, the 4-nitrophenylchloroformate solution was transferred into a 2000 L reactor containing dichloromethane solution of compound 1. The reaction mixture was heated to 40±5° C. (reflux) under nitrogen gas purge for 3 hrs. Representative TLC analysis confirmed completion of reaction (in-process TLC, no compound 1 remaining; 99:1 $CHCl_3$-MeOH). The solution was cooled to 30° C. and 460 kg of dichloromethane was distilled off under vacuum. The 2000 L reactor was charged with 520 kg of hexanes and the contents of the reactor were cooled to 0±5° C. and agitated for 4 hrs. The solid obtained was filtered through a GF Nutsche filter lined with a sheet of T-515 LF Typar filter and a sheet of Mel-Tuf 1149-12 filter paper. The filter cake was washed with 20 kg of hexanes and vacuum dried at 35° C. until constant weight was attained. The dry product was discharged (70.15 kg) with 98% yield. The product 2 was confirmed by $^1$H NMR and TLC analysis.

Step 2:

A 2000 L GL reactor was charged with compound 2 (64.4 kg, 1.0 eq.), anhydrous tetrahydrofuran (557 kg) and triethylamine (2.2 kg, 0.1 eq.). The charging line of the 2000 L GL reactor was rinsed with tetrahydrofuran (10 kg). The contents of the reactor were agitated for 25 mins, during which period a complete solution was obtained. A 200 L HP reactor was charged with N-Boc-p-phenylenediamine (38 kg, 1.0 eq.), tetrahydrofuran (89 kg) and agitated for 30 mins until a complete solution was obtained. The contents of the 200 L HP reactor were transferred to the 2000 L GL reactor containing compound 2 and then heated at 65±5° C. for 2 hrs. The reaction was deemed complete by HPLC after confirming the disappearance of starting material 2 when the amount of compound 2 remaining in the reaction mixture is <1%.

The contents of the 2000 L GL reactor were cooled to 20±5° C. and then charged with sodium methoxide (25% solution in methanol, 41.5 kg, 1.05 eq.) over 20 mins, while maintaining the temperature below 30° C. The charging lines were rinsed with tetrahydrofuran (10 kg). The contents were agitated at 25±5° C. for 4 hrs. In-process HPLC analysis confirmed the completion of the reaction when the amount of compound 3a remaining in the reaction mixture is <1%. To this reaction mixture was added filtered process water (500 kg) and the contents of the 2000 L GL reactor were distilled under vacuum into a clean 200 L GL receiver until 300 kg of solvent was distilled. The solids obtained were filtered using a GL Nutsche filter and washed with process filtered water until the color of the solid 3b was white to grayish.

The 2000 L GL reactor was charged with wet compound 3b filter cake, dioxane (340 kg) and the contents were agitated for 1 hr. The filterable solid obtained were filtered through a GL Nutsche filter with a sheet of T-515 LF Typar filter paper. The solid cake was blow dried for 2 hrs and then charged with dioxane (200 kg) into the 2000 L GL reactor. The contents were agitated for 10 mins and then charged with 4 N HCl in dioxane (914 kg) over 3 hrs while the internal temperature was maintained at below 30° C. The charging line was rinsed with additional dioxane (10 kg) and the contents of the reactor were agitated for 6 hrs at 25±5° C. The completion of the reaction was monitored by HPLC for the conversion of compound 3b to compound 3 (in process control shows compound 3b is <1% in the reaction mixture). The contents of the reactor were cooled to 5+5° C. for 2 hr and the solid obtained was filtered through a GL Nutsche filter followed by washing with dioxane (50 kg). The filter cake was blow-dried with 8±7 psi of nitrogen for 30 mins and the purity was analyzed by HPLC. The filtered solid was dried to a constant weight in vacuum oven at 45° C. for 48 hrs. The compound 3 (65.8 kg, actual yield 110.6%) was discharged and analyzed by $^1$HNMR and HPLC. $^1$H NMR (DMSO): δ 511.75 (s, 1H), 7.88 (dd, 1H), 7.32 (m, 4H), 7.21 (dd, 1H).

Step 3:

A 200 L HP reactor was charged with compound 3 (18 kg, 1.0 eq.) and pressurized with 100±5 psi of nitrogen. The nitrogen from the reactor was vented through the atmospheric vent line and the condenser valve was opened. Dimethyl sulfoxide was then charged into the reactor (>99.7%, 105 kg) under blanket of argon. The reactor contents were agitated at 22° C. (19-25° C.) for 15 mins and then maximum achievable vacuum was pulled on the 200 L HP reactor and all valves were closed. Using the established vacuum methylamine (33 wt % in absolute ethanol, 37.2 kg) was charged to the 200 L HP reactor at a rate that maintains the internal temperature at 25±5° C. A nitrogen blanket on the reagent solution was maintained during charging. After the charging line was rinsed with dimethyl sulfoxide (5 kg), the 200 L HP reactor condenser valve was closed and the reactor contents were heated to 110±5° C. The contents of the reactor were agitated for at least 5 hrs at 110±5° C. In-process HPLC taken after 5 hr 40 mins showed compound 3 content of 0.09%, indicating completion of the reaction (in-process specification requires amount of compound 3≤1%). The contents of the 200 L HP reactor were cooled to 25±5° C. While the 200 L reactor was cooling, all the valves of a 2000 L GL reactor were closed and process filtered water (550 kg) was charged. The contents of the 200 L HP reactor were transferred to the 2000 L GL reactor over 15 mins followed by rinsing the charging line with process filtered water (50 kg). The contents of the 2000 L GL reactor were agitated for 2 hrs at 5±5° C. The filterable solids obtained were filtered onto a GL nutsche filter fitted with Mel-Tuf 1149-12 filter paper under vacuum. The wet filter cake was discharged and transferred into pre-lined vacuum trays with Dupont's fluorocarbon film (Kind 100A) and special oven paper (KAVON 992) and transferred to the vacuum oven tray dryer. The oven temperature was set to 55°

C. and compound 4 was dried for 12 hrs to a constant weight. The product 4 was discharged (12.70 kg) in 76.5% yield (expected 85-95%). HPLC shows 98.96% purity and $^1$H NMR confirmed the structure for compound 4. $^1$H NMR (DMSO): δ 11.10 (s, 1H), 7.36 (d, 1H), 6.78 (d, 2H), 6.75 (m, 1H), 6.56 (d, 2H), 6.20 (d, 1H), 5.18 (d, 2H), 2.76 (d, 3H).

Step 4:

A 200 L HP reactor was charged with compound 4 (20.7 kg, 1.0 eq.), ethyl 5-chlorothiophene-2-ylsulfonylcarbamate (37.5 kg, 2.0 eq.>95%), dimethyl sulfoxide (>99%, 75 kg) and agitated for 15 mins. Maximum achievable vacuum was pulled and the 200 L HP reactor was heated at 65±5° C. for 15 hrs. In-process HPLC analysis of the representative sample from the reactor indicated <0.9% compound 4 remaining in the reaction mixture (in-process criteria for reaction completion is compound 4<1%). A 800 L reactor was charged with process filtered water (650 kg) and then the contents of the 200 L HP reactor were transferred to the 800 L reactor while the internal temperature was maintained below 25° C. The 200 L HP reactor was rinsed with dimethyl sulfoxide (15 kg) which was transferred to the 800 L reactor which was then agitated for 2 hrs at 5±5° C. The solid formed was filtered through a filter to a 200 L GL receiver under vacuum and the filter cake was rinsed with process filtered water (60 kg). HPLC analysis of a representative sample of the wet cake showed the purity of Compound A was <95%, indicating dichloromethane trituration was needed based on in-process control. The 800 L GL reactor was charged with the wet Compound A, dichloromethane (315 kg) and the contents were agitated for 3 hrs. The solid was filtered through GL nutsche filter lined with 1 sheet of T515 LF TYPAR filter under vacuum. The filter cake was washed with dichloromethane (50 kg) and the cake was blow dried with 8±7 psi of nitrogen for 15 mins. The filter cake was transferred into pre-lined vacuum trays with Dupont fluorocarbon film (Kind 100A) and then dried in the vacuum oven tray dryer at 60° C. for 12 hrs. The dried Compound A was isolated (33.6 kg, 93% yield) with HPLC purity of 93.5% and 4.3% of sulfonamide. $^1$H NMR confirmed the structure for Compound A. $^1$H NMR (DMSO): δ 11.20 (s, 1H), 9.15 (s, 1H), 7.68 (d, 1H), 7.42 (d, 2H), 7.36 (d, 1H), 7.26 (m, 1H), 7.16 (d, 2H), 6.78 (m, 1H), 6.24 (d, 1H), 2.78 (d, 3H).

Step 5:

A 800 L GL reactor was charged with acetonitrile (134 kg), WFI quality water (156 kg) and the contents was agitated for 5 mins. To this then charged Compound A (33.6 kg, 1.0 eq.) and the reaction mixture was a suspension at this point. The suspension was charged with aqueous solution (WFI water, 35 kg) of potassium hydroxide (4.14 kg, 1.15 eq., >85%) at a rate that maintained the internal temperature at below 30° C. The charging lines were rinsed with WFI quality water (2 kg) and the 800 L GL reactor contents were heated to 50±5° C. for 1 hr. The contents were then filtered hot through a bag filter, then a seven cartridge 0.2μ polish filter to clean HDPE drums. The hot filtration system was maintained through out the filtration process so no material crashed out of the solution. The 800 L GL reactor jacket was cooled to 25±5° C. before the 800 L GL reactor was rinsed with a pre-mixed solution of acetonitrile (8.5 kg) and WFI quality water (10 kg) through the filter system into the drums labeled as Compound A hot filtration. Using the pressure vessel the 800 L GL reactor was rinsed with WFI quality water (20 kg) followed by acetone (20 kg) then blow dried with nitrogen (3+2 psi). The 800 L GL reactor bottom valve was closed and 20+10 inches Hg of vacuum was pulled, then the contents of the drums labeled as Compound A hot filtration was charged to the reactor. The 800 L GL reactor contents were cooled to 20±5° C. and then using a polish filter, the reactor was charged with methanol (373 kg, >99%) while maintaining the internal temperature below 30° C. The contents of the 800 L GL reactor were cooled to 15±5° C. followed by agitation of the contents for 12 hrs at this temperature. During this time the filterable solids were filtered through a clean filter apparatus into a clean 200 L GL receiver followed by pressurizing the reactor, pulling 20+10 inches Hg of vacuum on the filter/receiver and filtered the contents. The filter cake was washed with methanol (30 kg) and blow dried with 8+7 psi of nitrogen for 10 mins. The vacuum oven tray dryer temperature was set to 80° C. prior to loading the wet cake of the salt Formula I. The wet filter cake was transferred into the pre-lined vacuum trays with Dupont's fluorocarbon film (Kind 100A) and the special oven paper (Kavon Mel Tuf paper) and dried in the vacuum oven tray dryer at an oven temperature of 80° C. to a constant weight (constant weight is defined as tray reading at least 1 hr apart having the same weight within +50 g). A representative sample was analyzed (residual solvent specifications for API) and showed that residual solvents met the specifications. The final API was subjected to equilibration with water (5-6%) for 12 hrs with a tray of WFI quality water present, then thoroughly turned and allowed to stand for an additional 12 hrs and finally subjected to KF (Karl Fischer) water analysis (5.5% water content). The salt Formula I was transferred (21.80 kg, 60.6% yield) to double heavy-duty poly bags and stored in secondary containment. HPLC showed purity of 99.7% for and $^1$H NMR confirmed the structure of Compound A. $^1$H NMR (DMSO): δ 11.14 (s, 1H), 8.60 (s, 1H), 7.48 (m, 2H), 7.35 (d, 1H), 7.22 (d, 1H), 6.95 (m, 3H), 6.75 (m, 1H), 6.22 (d, 1H), 2.78 (d, 3H).

Additional methods of preparation and analysis of Compound A and its salt forms are described in U.S. Patent Application Publication US 2007/0123547, filed Nov. 3, 2006, the contents of which are incorporated herein by reference in its entirety.

Example 2

Preparation of Betrixaban

Scheme 2

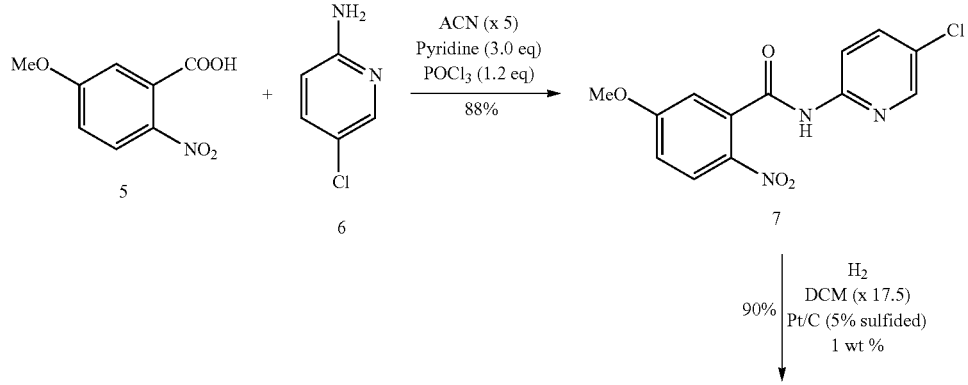

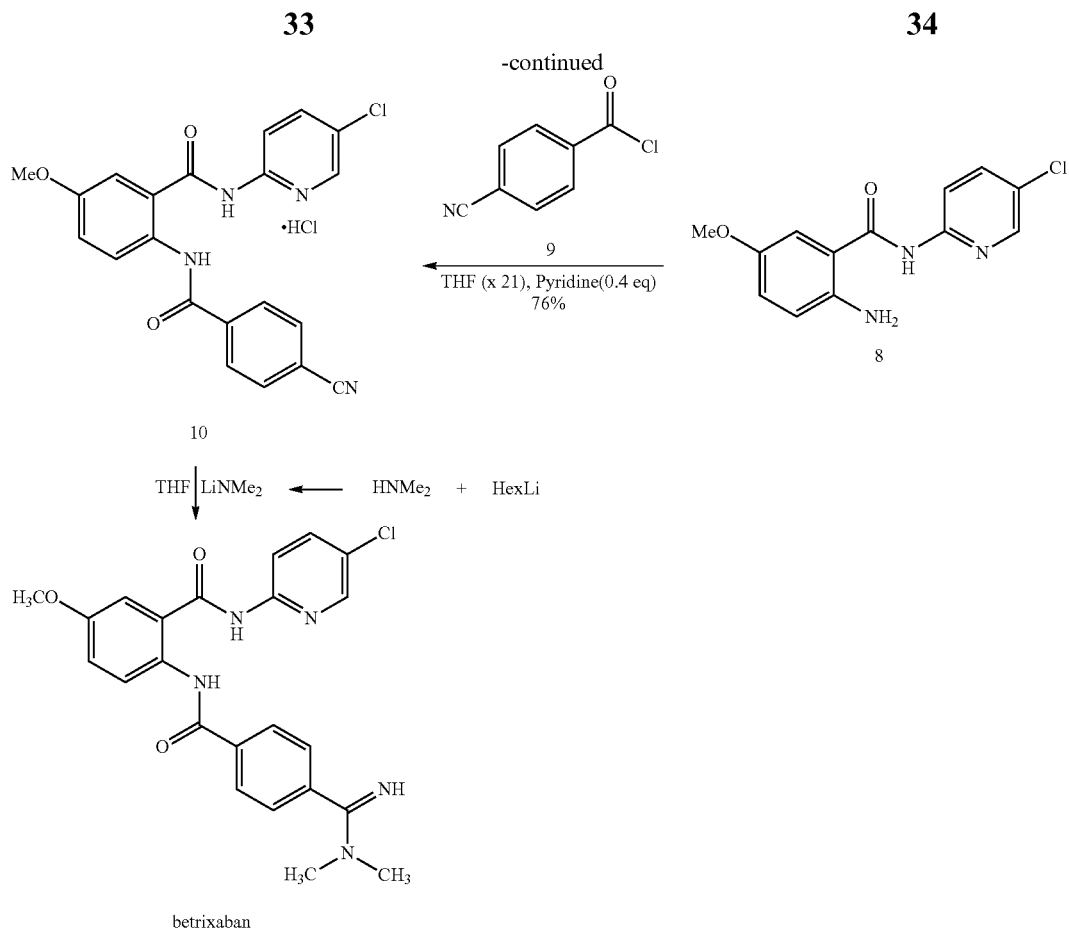

Step 1:

5-Methoxy-2-nitrobenzoic acid (5) (25.0 kg, 1.0 eq.), 2-amino-5-chloropyridine (6) (16.3 kg, 1.0 eq.), and acetonitrile (87.5 kg, 3.5 parts) were charged to a 380 L GLMS reactor. The reaction mixture was adjusted to 22° C. (19 to 25° C.) and anhydrous pyridine (30.0 kg, 3.0 eq.) was added. The pump and lines were rinsed forward with acetonitrile (22.5 kg, 0.9 parts), and the reactor contents were adjusted to a temperature of 19-22° C. Phosphorous oxychloride (23.3 kg, 1.20 eq.) was charged to the contents of the reactor via a metering pump, while maintaining a temperature of 25° C. (22-28° C.). The metering pump and lines were rinsed forward with acetonitrile (12.5 kg, 0.5 parts), while keeping the temperature at 25° C. (22-28° C.). The reaction mixture normally turned from a slurry to a clear solution after the addition of about ⅓ of the POCl₃. At the end of the addition, it became turbid. After complete addition, the reaction mixture was agitated at 25° C. (22-28° C.) for ca. 1 hr, at which time HPLC analysis confirmed reaction completion. The solution was cooled to 15° C. (12-18° C.) and drinking water (156.3 kg, 6.25 parts) was charged slowly while keeping reaction temperature between 12 and 30° C. The reaction mixture was then adjusted to 22° C. (19 to 25° C.) and agitated for ca. 5 hrs until exotherm ceased. Formation of a slurry was visually confirmed and the contents of the reactor were filtered onto a pressure nutsche fitted with a filter cloth. The reactor, pump, and lines were washed forward onto the pressure nutsche with two portions of drinking water (62.5 kg, 2.5 parts each). The filtrate had a pH value of 7. The product (41.8 kg) was dried under vacuum with a maximum temperature of water bath (to heat dryer jacket) of 50° C. After ca. 12 hrs, in-process LOD analysis indicated a solvent content of 0.72%. The dry product 7 was discharged (34.4 kg) with 88.2% yield and 99.1% purity by HPLC.

Step 2:

To a 780 L Hastelloy reactor, compound 7 (33 kg, 1.0 eq), 5% platinum carbon (sulfided, 0.33 kg, 0.010 parts) and dichloromethane (578 kg, 17.5 parts) were charged. Agitation was started and reactor contents were adjusted to 22° C. (19 to 25° C.). The reactor was pressurized with ca. 30 psi hydrogen and the reaction mixture gently heated to 28° C. (25-31° C.). Hydrogenation of the reactor contents was performed under ca. 30 psi at 28° C. (25 to 31° C.; maximum 31° C.) until the reaction was complete by HPLC. After 16.5 hrs, the reaction was deemed complete after confirming the disappearance of starting material (0.472%). The contents of the reactor were circulated through a conditioned celite pad (0.2-0.5 kg celite conditioned with 20-55 kg dichloromethane) prepared in a 8" sparkler filter to remove the platinum catalyst. The reactor and celite bed were rinsed forward with two portions of dichloromethane (83 kg, 2.5 parts each). The filtrate was transferred to and concentrated in a 570 L GLMS reactor under a atmospheric pressure to ca. 132 L (4 parts volume). Ethanol (69 kg, 2.1 parts) was charged and concentration continued under atmospheric pressure to ca. 99 L (3 parts volume). In-process NMR indicated that the dichloromethane content was 39%. Ethanol (69 kg, 2.1 parts) was charged again and concentration continued again to ca. 99 L (3 parts volume). In-process NMR indicated that the dichloromethane content was 5%. The reaction mixture was then adjusted to 3° C. (0 to 6° C.), agitated for ca. 1 hr, and the resulting slurry filtered onto a jacketed pressure nutsche fitted with a filter cloth. The reactor, pump, and lines were rinsed forward with cold (3° C. (0-6° C.)) ethanol (26 kg, 0.8 parts). The wet filter cake (36.6 kg) was dried under vacuum at 40-50° C. with a maximum temperature of water bath (to heat dryer jacket) of 50° C. LOD analysis after 12.5 hrs indicated solvent content was at 0.1%. The dry product 8 was discharged (26.4 kg) in 89.5% yield. HPLC showed 98.4% purity, with dechlorinated impurity at 0.083%.

Step 3:

To a 780 L Hastelloy reactor, was charged 4-cyanobenzoyl chloride (9) (17.2 kg, 1.1 eq.) and THF (92 kg, 3.5 parts). Reactor contents were agitated at 22° C. (19 to 25° C.) until all of the solids had dissolved. The resulting solution was transferred to a lower receiver and the reactor was rinsed forward with THF (26 kg, 1 part). Compound 8 (26.4 kg, 1 eq.), THF (396 kg, 15 parts) and pyridine (2.90 kg, 0.4 eq.) were charged to a clean reactor. The pump and lines were rinsed forward with THF (34 kg, 1.3 parts). Via a metering pump, the 4-cyanobenzoyl chloride/THF solution was charged to the reactor, keeping the temperature at ≤30° C. and rinsing forward with THF (ca. 10 kg). The resulting yellow-colored slurry was agitated at 22° C. (19 to 25° C.) for ca 2 hrs. In-process HPLC taken after 2 hrs showed a compound 8 content of 0%, indicating completion of the reaction. The slurry was filtered onto a pressure nutsche fitted with a filter cloth. The reactor, pump, lines, and wet cake were rinsed with three portions of ethanol (ca. 15 kg each). The wet filter cake was discharged (65.4 kg) and transferred back to the reactor for slurry wash in ethanol (317 kg, 12 parts) at 22° C. (19 to 25° C.) for ca. 1 hr. The slurry was filtered onto the pressure nutsche and the reactor, pump, lines, and wet filter cake were rinsed with two portions of ethanol (ca. 15 kg each) and two portions of THF (ca. 15 kg each). The wet filter cake was dried under vacuum with a maximum temperature of warm glycol bath (to heat the reactor jacket) of 40° C. After 14.5 hrs of drying, LOD was 0.75%. The dried material was milled (screen 0.125") to give 31.8 kg of compound 10, which was dried under vacuum for another 10.5 hrs. LOD after drying was 1.8%, and the product was discharged (31.5 kg) in 74.8% yield (expected 60-90%). HPLC showed 100% purity.

Step 4:

A slurry of compound 10 (455 g, 1.0 eq.) in THF (4.67 kg, 10.3 parts) was prepared and adjusted to <10° C. Lithium dimethyl amide was prepared as follows: hexyllithium (2.3 N/hexane, 2.45 L, 5.5 eq.) was added to dimethylamine solution (2 N/THF, 2.8 L, 5.5 eq.) maintaining <10° C. The lithium dimethyl amide solution was charged into the slurry containing the compound 10 keeping the pot temperature of <10° C. The reaction progress was monitored by in-process HPLC which confirmed that the amount of compound 10 was <1.0%. A buffer solution of $NaHCO_3$ (490 g, 1.1 parts, 5.7 eq.) and $Na_2CO_3$ (490 g, 1.1 parts, 4.5 eq.) in deionized water (6.6 kg, 14.51 parts) was prepared, and above reaction mixture was transferred to this aqueous solution maintaining <5° C. The product precipitated out and the resulting slurry was adjusted to 20° C. over a period of 12 hrs. The solid was filtered, and the resulting wet cake was washed with 3.5 kg (7.7 parts) of deionized water. The solid was filtered off using a coarse frit glass bench filter, and rinsed forwarded with cold (0-5° C.) absolute ethanol (628 g, 1.4 parts). The product betrixaban was dried at 30-35° C. Dry product was obtained in 458 g (73% yield).

Example 3

Combination of Compound A and Betrixaban in a Perfusion Chamber Thrombosis Assay (I)

The real time perfusion chamber assay couples the features of animal thrombosis models that use intravital microscopy to those of perfusion chamber technology in order to produce an assay suited to monitoring drug activity in clinical trials. This assay perfuses whole blood through capillaries at arterial rates of shear, exposing the blood to thrombogenic type III collagen. Platelets are labeled with a fluorescent dye (rhodamine 6 G) prior to perfusion such that analysis of the thrombus deposition can be performed by measurement of fluorescence intensity inside the perfusion chamber. Quantification is performed by analysis of the thrombus height (fluorescence intensity (number of pixels)/total area ($\mu m^2$)).

Figure 2:
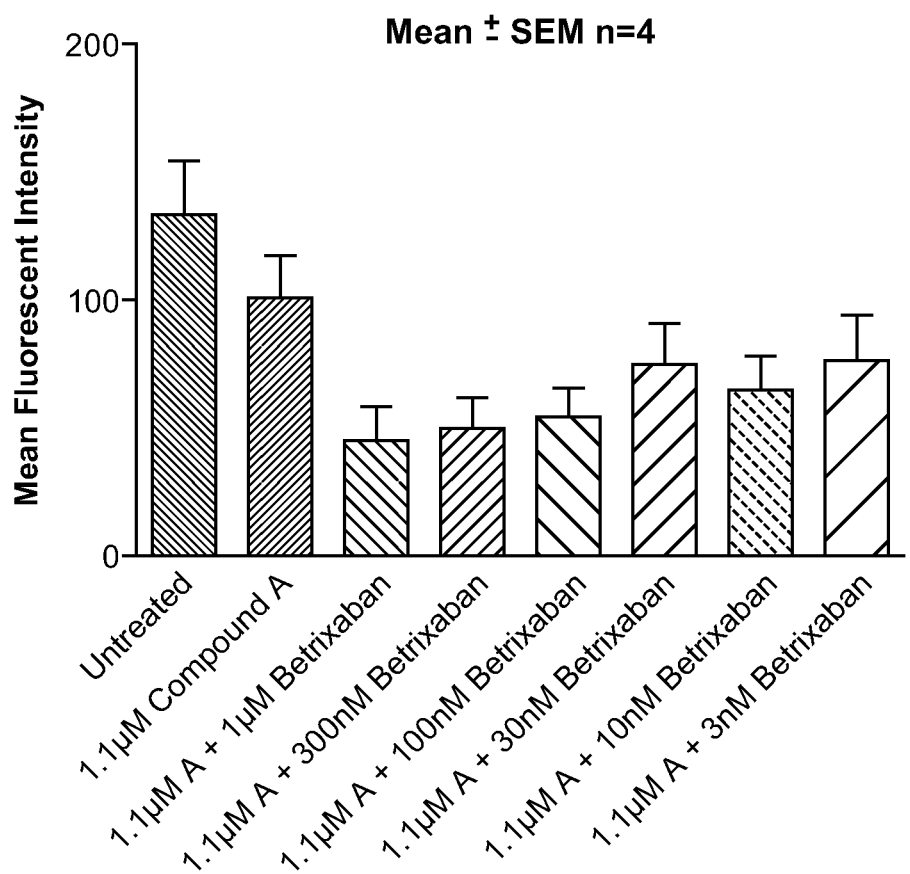
FIG. 2 shows the dose responsive inhibition of thrombosis by a combination of a fixed concentration of Compound A with increasing concentrations of betrixaban upon perfusion of whole human blood over a collagen coated surface where the concentration of betrixaban varies from 3 nM to 1.1 μM.

Compound A was tested in this assay at a concentration capable of generating equivalent levels of inhibition of ADP induced platelet aggregation in human platelet rich plasma as targeted by clopidogrel, a widely used antiplatelet agent whose antithrombotic activity is mediated by inhibition of the platelet $P2Y_{12}$ receptor. As shown in FIG. 1, treatment of blood with Compound A at 1.1 µM, while capable of significant inhibition of platelet aggregation produced only partial inhibition of thrombosis (23%±14%, p>0.05, n=4). Addition of betrixaban to blood already treated with Compound A produced significant inhibition of thrombosis (68%±3%, 59%±14%, and 57%±11% inhibition at 1 µM, 300 nM and 100 nM betrixaban respectively, p<0.01, n=4). FIG. 2 demonstrates the dose dependent inhibition of thrombosis at betrixaban concentrations between 1 µM and 3 nM.

Example 4

Combination of Compound A and Betrixaban in a Real-Time Thrombosis Assay (II)

Figure 3:
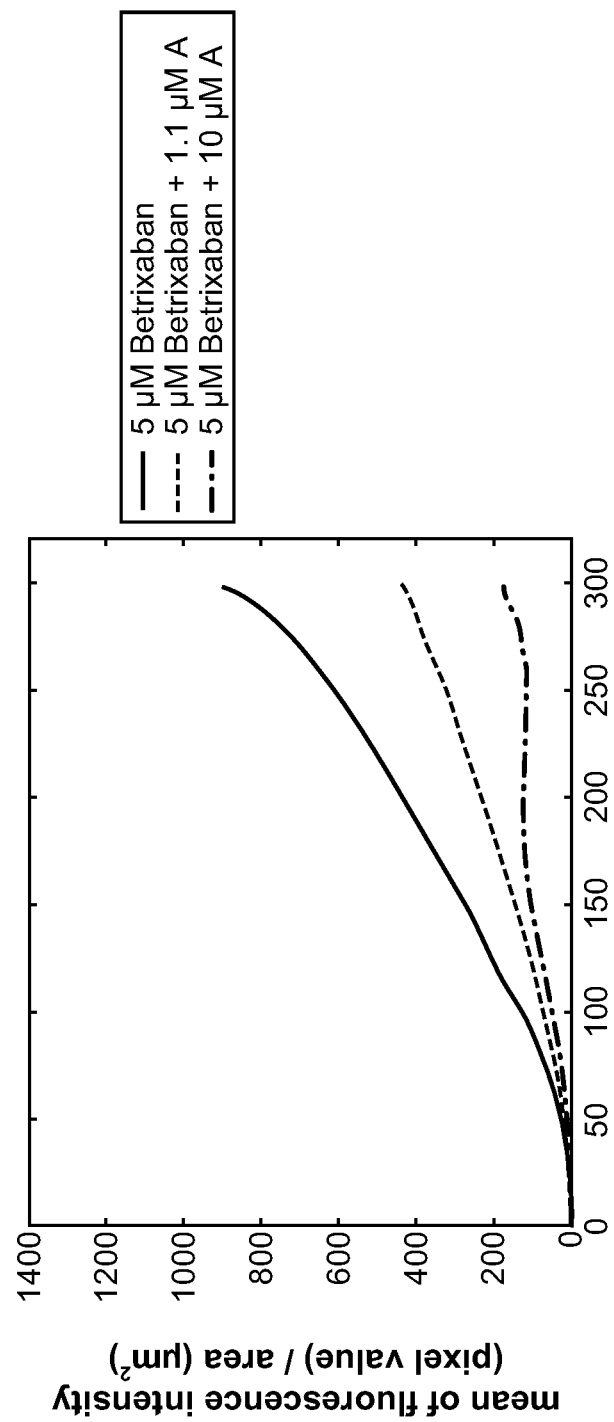
FIG. 3 shows dose responsive inhibition of thrombosis by a combination of increasing concentrations of Compound A with a fixed concentration of betrixaban upon perfusion of whole human blood over collagen coated surface.

Blood was collected by venipuncture from healthy volunteers into 5 µM betrixaban. Increasing concentrations of Compound A were added in vitro. Following 20 mins incubation, blood was perfused through the collagen coated capillary (type III collagen, 1600 $sec^{-1}$). As seen in FIG. 3, increasing concentrations of Compound A demonstrated dose responsive inhibition of thrombosis, with 10 µM of Compound A resulting in a single monolayer of platelets.

Example 5

Combination of Compound A and Betrixaban in a Thrombin Generation Assay

Whole blood from healthy volunteer donors was collected by venipuncture and drawn into 3.2% trisodium citrate (Vacutainer, Becton Dickinson) for anticoagulation. Platelet rich plasma was prepared by centrifugation and the platelet count was adjusted to 150,000/µL. In a 96 well plate, platelets were activated by addition of convulxin (200 ng/mL) and incubation at 37° C. for 3 mins. Subsequent to platelet activation, thrombin generation was initiated by addition of 23 pM tissue factor (Innovin, Dade Behring) and 15 mM calcium. Thrombin activity was monitored by cleavage of the specific fluorogenic substrate (Z-gly-gly-arg-AMC, Bachem) in a fluorescence plate reader.

Figure 4:
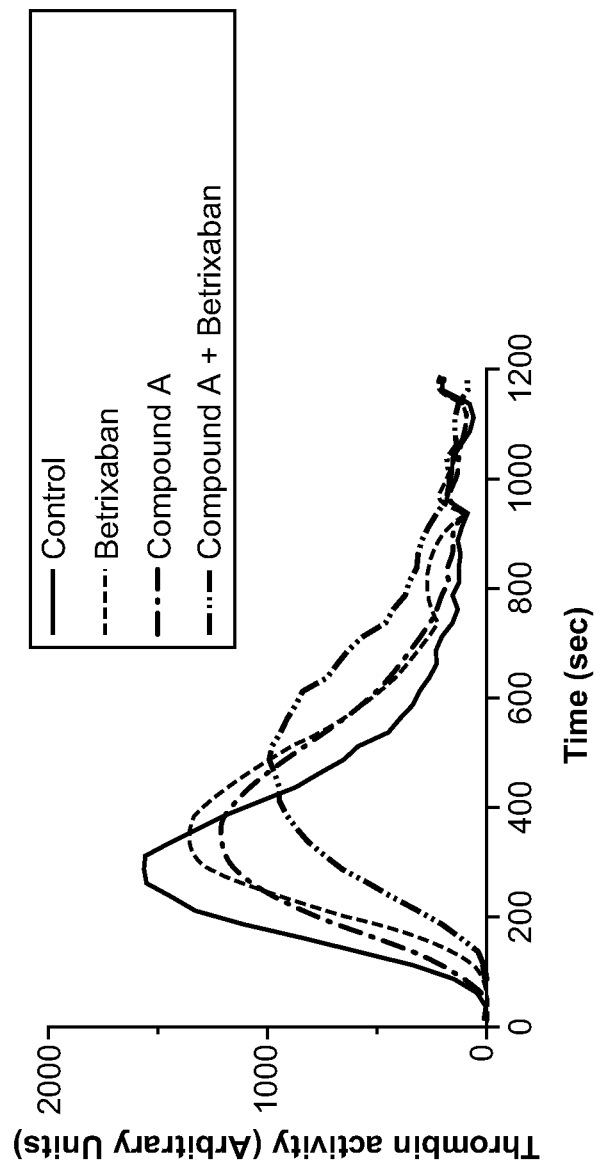
FIG. 4 shows combined inhibition of platelet mediated thrombin generation by the combination of inhibition of the platelet $P2Y_{12}$ receptor by Compound A and coagulation by a factor Xa inhibitor, betrixaban.

In platelets derived from human donors, half maximal inhibition of ADP induced platelet aggregation was achieved at a Compound A concentration of 4.7±5.1 µM (n=19). For the factor Xa inhibitor betrixaban, a concentration of 31.25 nM was adequate for equivalent inhibition of thrombin generation as that achieved by a therapeutic anticoagulant (Pentasaccharide fondaparinux). As shown in FIG. 4, even when Compound A was used at a concentration capable of maximal inhibition of platelet aggregation (10 µM), there was a substantial level of thrombin generation in this ex vivo system.

Similar results of thrombin generation were obtained by using the factor Xa inhibitor betrixaban at its therapeutic concentration. However, a combination of the two agents provided greater inhibition of thrombin production. Since thrombin activity is a mediator of thrombotic conditions, the combination of the two agents has the potential to produce superior activity than each of the single agents alone.

Example 6

Combination of Compound A and an Anti-Factor XI Antibody (I)

Figure 5:
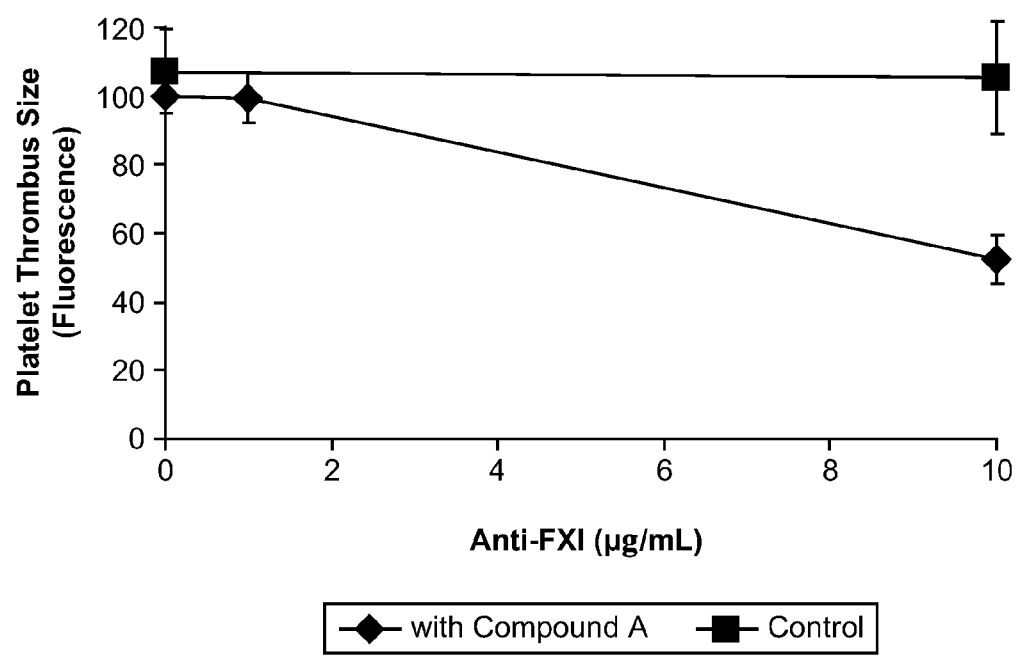
FIG. 5 shows the combined inhibitory effect of a coagulation factor XI inhibitor (an anti-factor XI antibody) and Compound A on platelet thrombus formation under conditions where either single agent alone did not show inhibition.

In this example, non-anticoagulated whole blood was collected from healthy volunteers, and rhodamine 6G (which fluorescently labels platelets), along with an antibody to factor XI (Hemetech) and Compound A, before perfusing through a collagen-coated capillary (type I collagen) at arterial shear rates (1000 s$^{-1}$). After perfusion the size of the platelet thrombus was measured by fluorescence. As shown in FIG. 5, the anti-factor XI antibody alone did not reduce thrombus size at up to 10 µg/mL concentration under the assay conditions. Compound A alone had no significant effect on platelet thrombus size at 10 µM in this assay. However, when increasing concentrations of a factor XI antibody were combined with 10 µM of Compound A, a dose proportional inhibition of thrombus size was observed, reaching a maximum of 50% inhibition at 10 µg/mL of the factor XI antibody.

Example 7

Combination of Compound A and an Anti-Factor XI Antibody (II)

Figure 6:
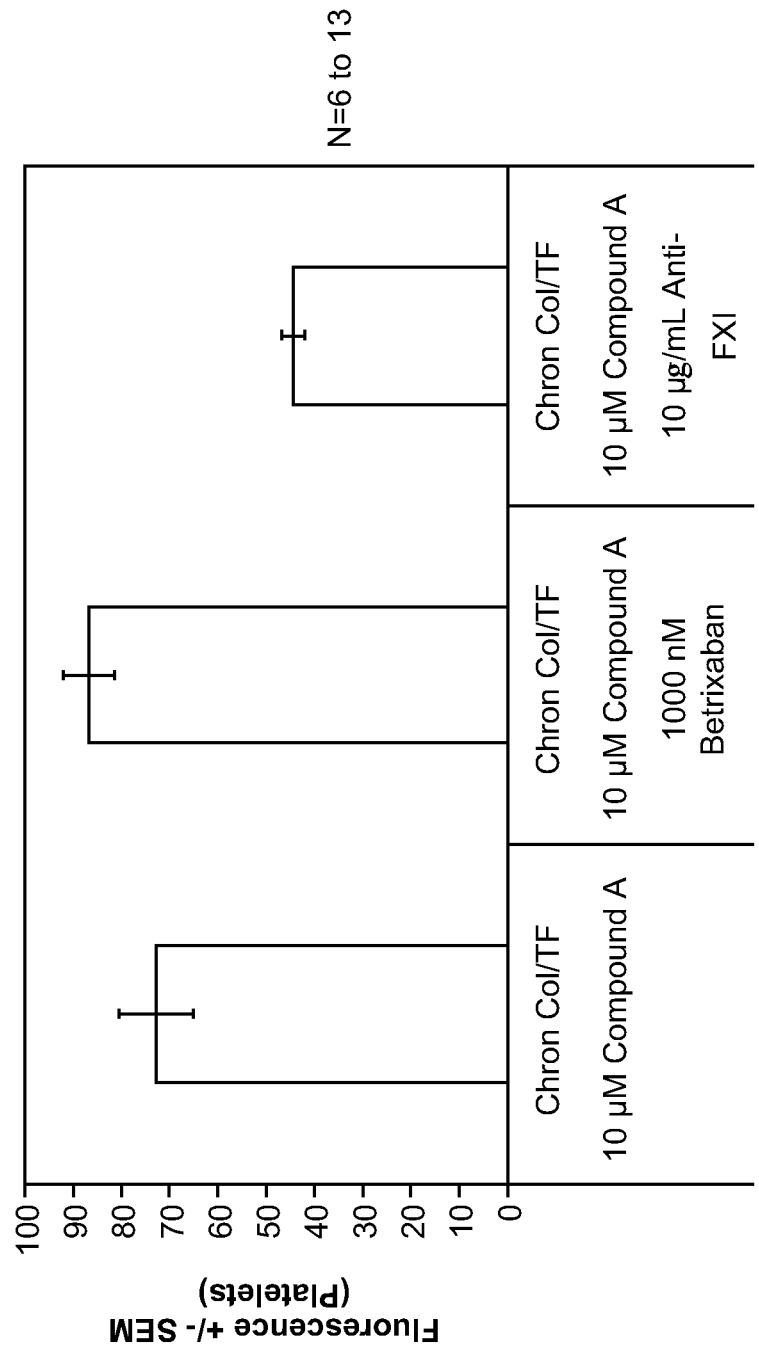
FIG. 6 shows the combined inhibitory effect of Compound A and a coagulation factor XI inhibitor (anti-factor XI antibody) on platelet thrombus formation on a collagen: tissue factor surface, whereas Compound A alone or a combination of Compound A and betrixaban did not show inhibition.

Capillaries were coated with a combination of type I collagen and tissue factor (1/100 ratio of collagen to Innovin (Dade-Behring). Non-anticoagulated blood was combined with rhodamine 6G, 10 µM of Compound A and either betrixaban or an antibody against factor XI before perfusion through the capillary. As shown in FIG. 6, the combination of Compound A and the factor XI antibody was able to produce significantly more inhibition of thrombus formation than Compound A alone or the combination of Compound A and betrixaban.

Example 8

Combination of Compound A and Bivalirudin, a Direct Thrombin Inhibitor

Figure 7:
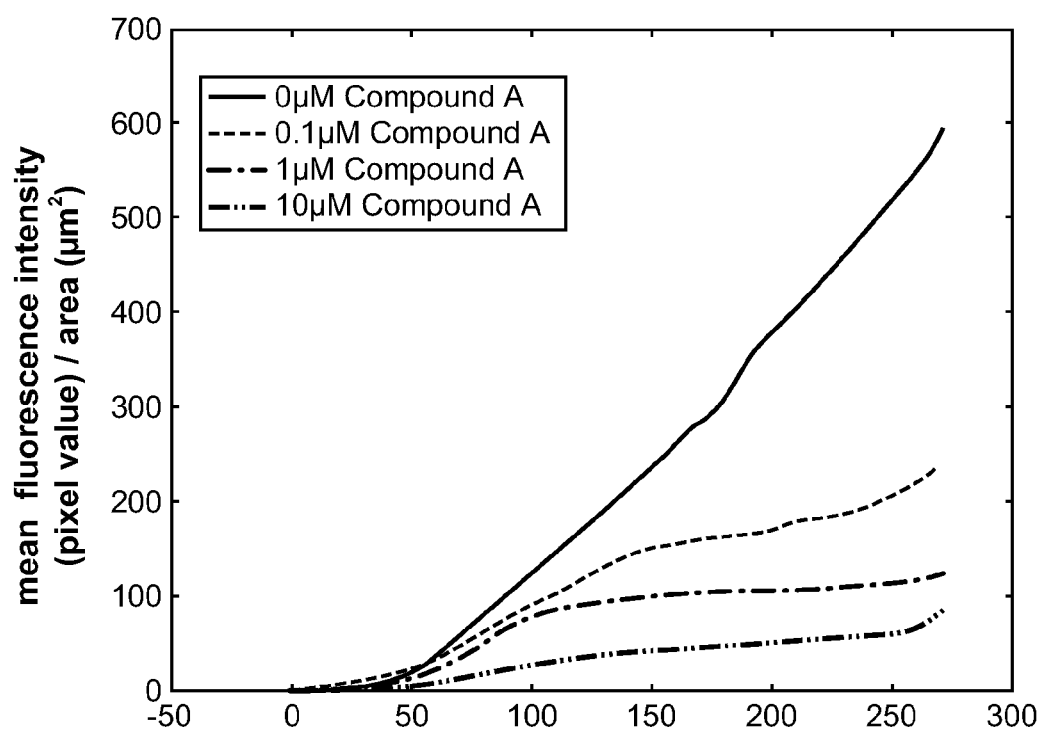
FIG. 7 shows the combined inhibitory effect of increasing concentrations of Compound A with a direct thrombin inhibitor bivalirudin (12 μg/mL) on thrombus formation under arterial shear conditions.

As an example of additive antithrombotic benefit achieved when Compound A was combined with a direct thrombin inhibitor, such as bivalirudin, in the following assay, blood was collected in 12 µg/mL bivalirudin (standard therapeutic concentration), incubated with various concentrations of Compound A (0.1, 1 or 10 µM) for 20 mins in the presence of rhodamine 6G (which fluorescently labels platelets), followed by perfusion through a glass capillary coated with collagen (type III) at a fixed shear rate (1600 s$^{-1}$). Under these conditions, bivalirudin alone did not significantly inhibit the thrombotic process; however, a dose-dependent inhibition of thrombosis was observed when increasing amounts of Compound A are present in combination with bivalirudin. FIG. 7 illustrates the combined antithrombotic benefit achieved by the combination of Compound A and bivalirudin.

Example 9

Combination of P2Y$_{12}$ Antagonist Compound A and Aspirin, a Cyclooxygenase Inhibitor, and a Factor Xa Inhibitor Using a real-time perfusion chamber assay to assess the thrombotic profile of healthy donors where human blood was collected by venipuncture from aspirinated donors (81 mg or 325 mg of aspirin daily for 3 days), the additive antithrombotic benefit of Compound A on top of aspirin was assessed. In this assay, glass capillaries were coated with type I collagen, and human whole blood (incubated for 20 mins with rhodamine-6G, which fluorescently labels platelets) collected in a factor Xa inhibitor, C921-78 (see Betz A, Wong P W, Sinha U Inhibition of factor Xa by a peptidyl-alpha-ketothiazole involves 2 steps: evidence for a stabilizing conformational change. *Biochemistry* 1999; 38: 14582-14591, incorporated herein by reference in its entirety), was perfused through the capillary at a fixed sheer rate (1600 sec$^{-1}$). During perfusion, the extent of thrombosis was quantified by measurement of mean fluorescence intensity/area (µm$^2$), which is a measure of platelet deposition on the collagen surface.

Figure 8:
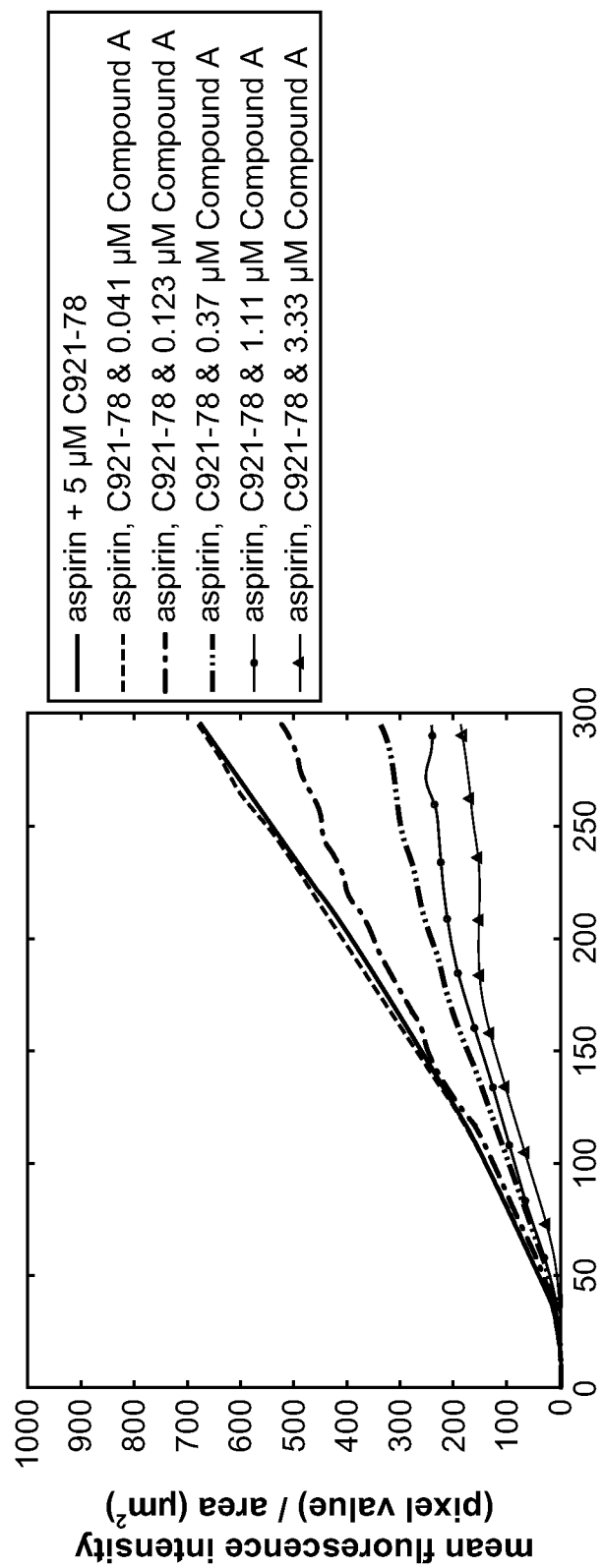
FIG. 8 shows the combined effect of Compound A and aspirin, in the presence of a factor Xa inhibitor (5 μM of C921-78 (see Betz A., Wong P. W., Sinha U. Inhibition of factor Xa by a peptidyl-alpha-ketothiazole involves 2 steps: evidence for a stabilizing conformational change. *Biochemistry* 1999; 38: 14582-14591, incorporated herein by reference in its entirety)) on inhibition of the thrombotic process in a whole blood perfusion chamber assay.

As shown in FIG. 8, increasing concentrations of Compound A, when added to whole blood in vitro (incubated for 15 mins prior to perfusion through the capillary), inhibit the thrombotic process in a dose-dependent manner. A concentration of 0.37 µM Compound A has statistically significant additional antithrombotic benefit in the presence of aspirin and a factor Xa inhibitor, whereas this concentration of the P2Y$_{12}$ antagonist alone has no detectable antithrombotic activity in the absence of aspirin.

Example 10

Combination of Compound A and Ifetroban, a TP Antagonist, and a Factor Xa Inhibitor Similar to the previous example, the combination of Compound A and a TP antagonist (e.g. ifetroban) and a factor Xa inhibitor showed additive antithrombotic benefit.

Figure 9:
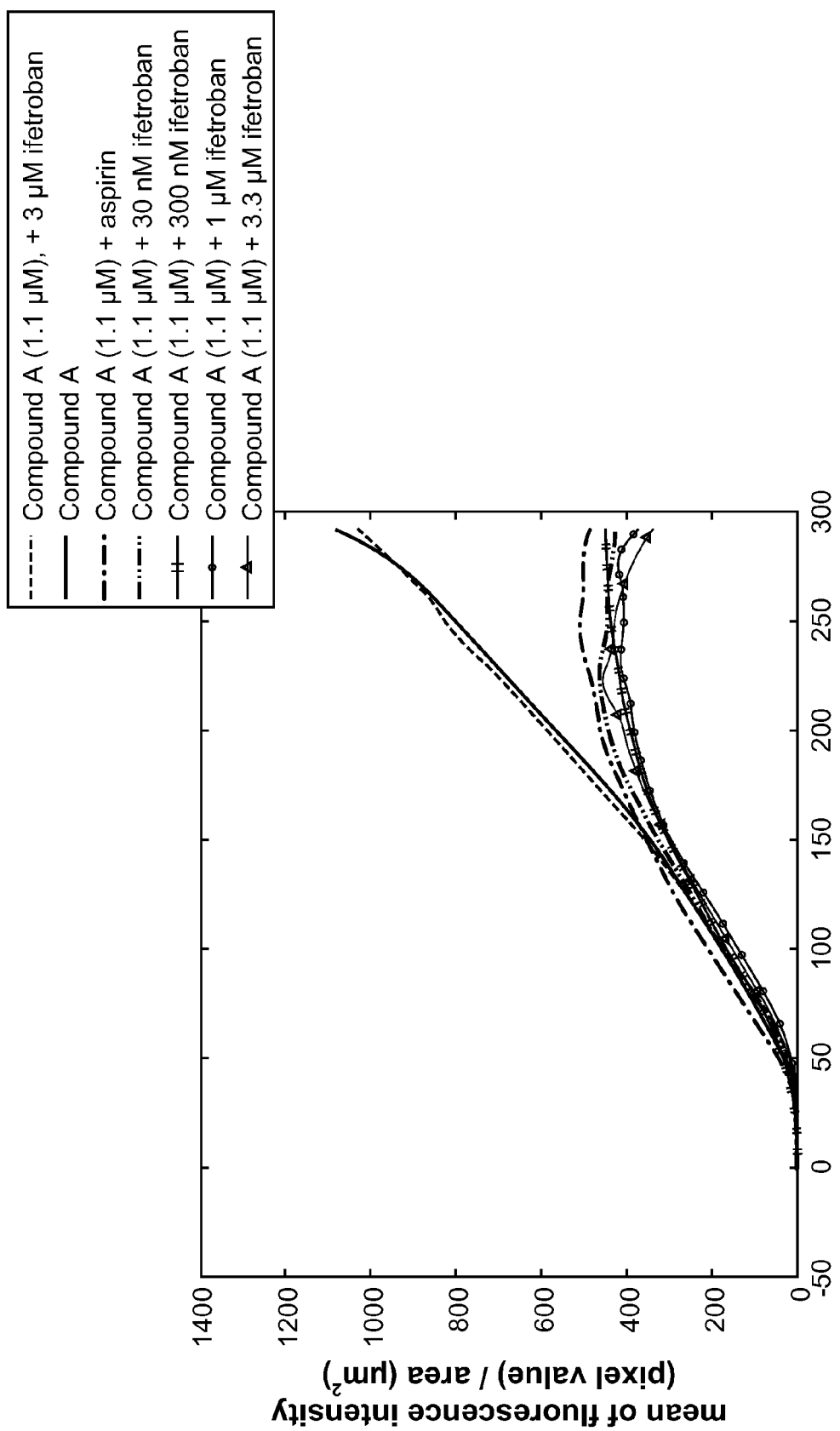
FIG. 9 shows combined effect of $P2Y_{12}$ inhibition by Compound A and inhibition of TP receptors by ifetroban in the presence of a factor Xa inhibitor (5 μM of C921-78) on inhibition of the thrombotic process in a whole blood perfusion chamber assay.
Figure 10:
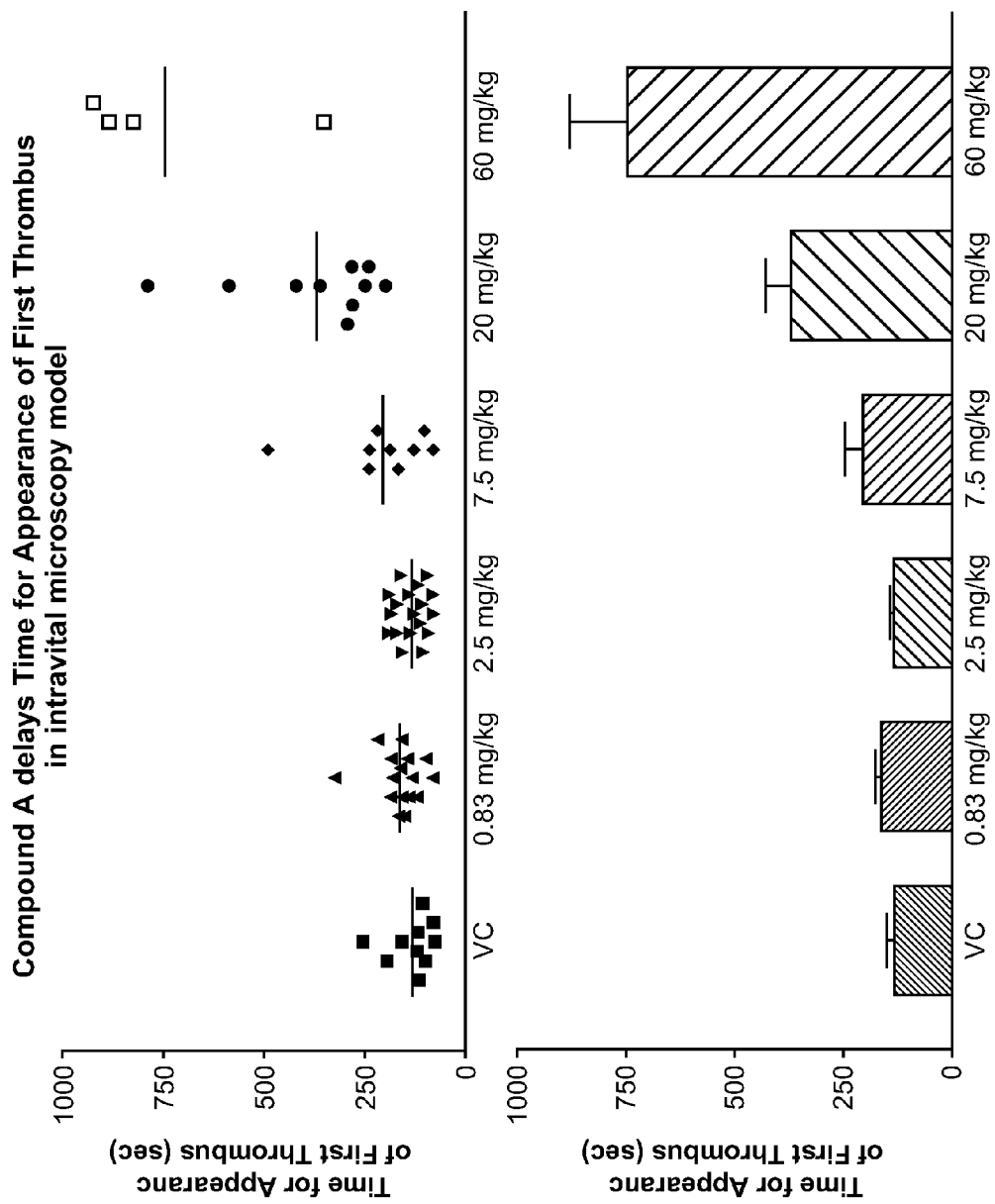
FIGS. 10-13 shows the effect of Compound A in an intravital microscopy model.
Figure 11:
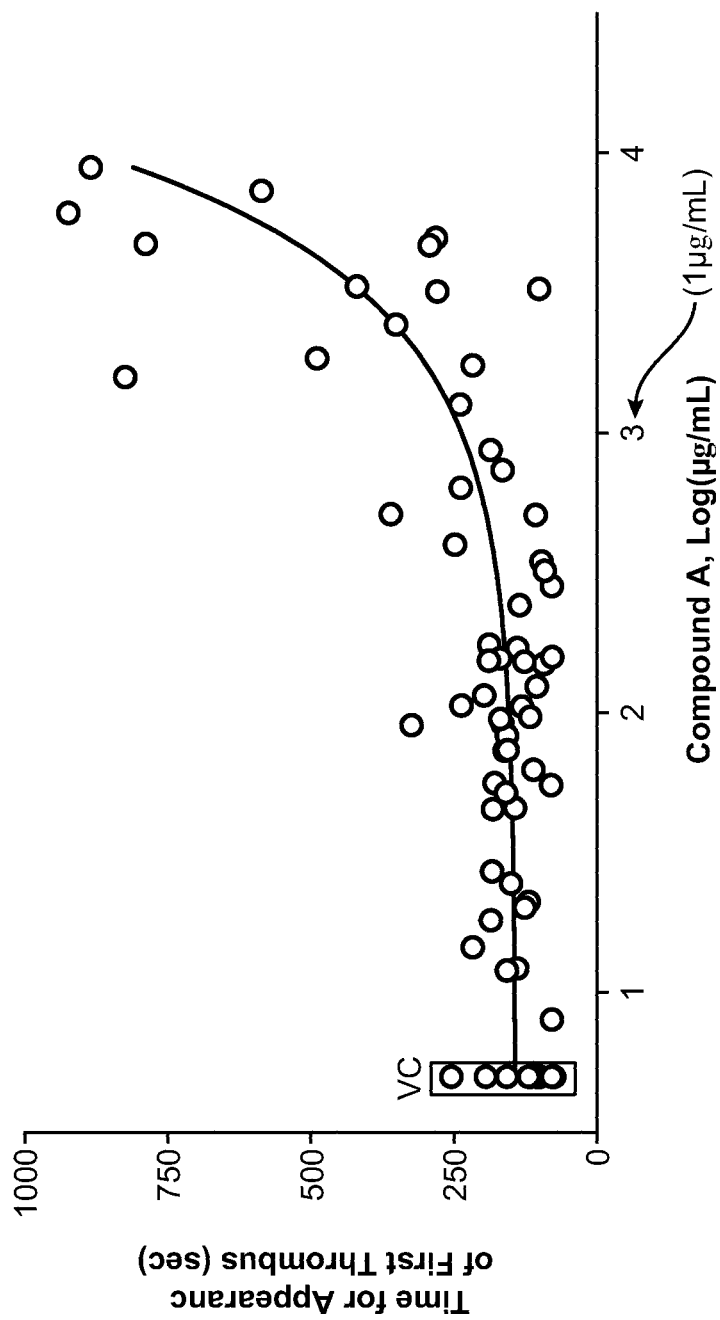
Figure 12:
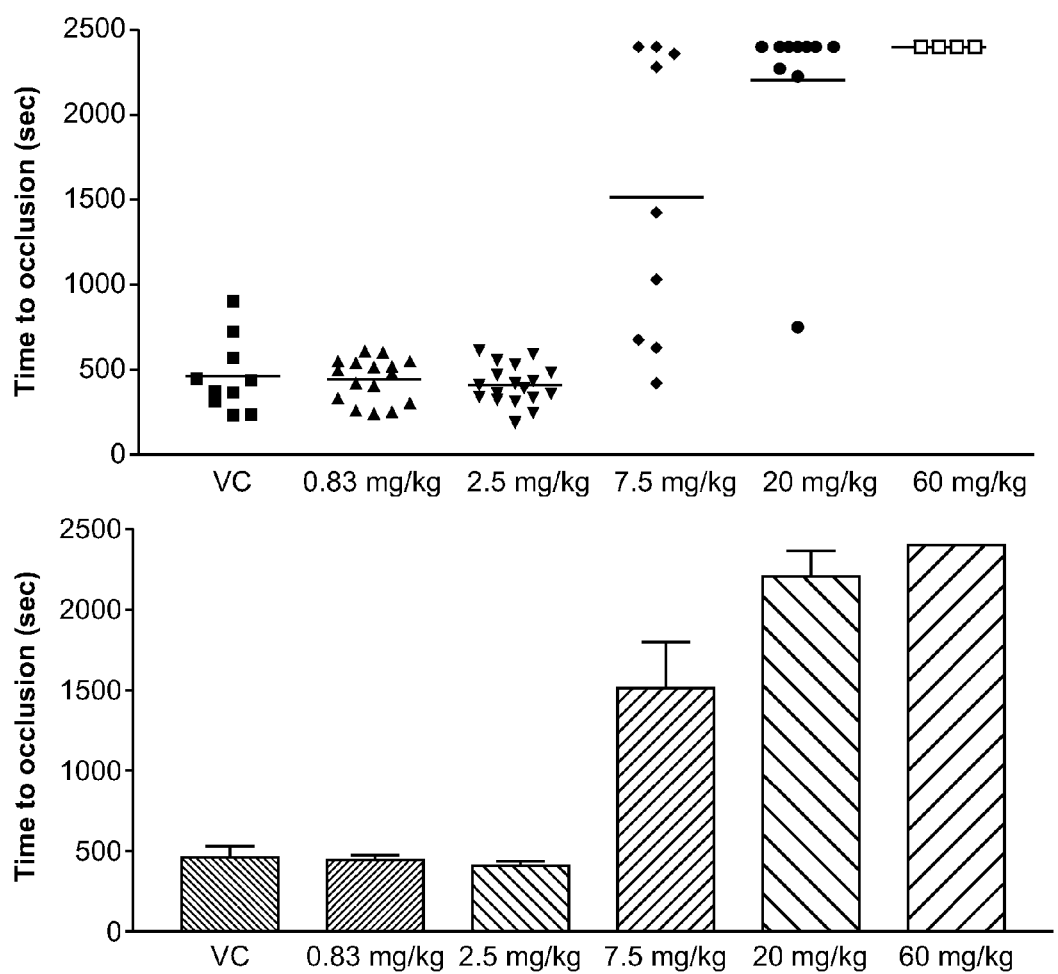

In this example, blood was collected from healthy volunteers by venipuncture into a factor Xa inhibitor C921-78 (see above). Compound A was added to the blood sample at a concentration (1.1 µM) that mimics the inhibitory effects of clopidogrel in this assay. As seen in FIG. 9, when increasing concentrations of ifetroban are added to whole blood and preincubated with Compound A (1.1 µM) for 30 mins prior to perfusion of blood through the collagen-coated capillary (type I collagen, 1600 sec$^{-1}$), a dose-responsive inhibition of thrombosis was observed, with the combination of 1.1 µM of Compound A and 30 nM of ifetroban in the presence of a factor Xa inhibitor giving the same level of inhibition as clopidogrel plus aspirin or Compound A plus aspirin.

Example 11

Combination of Compound A and a Factor Xa Inhibitor in a Real-Time Thrombosis Assay Blood is collected by venipuncture from healthy volunteers into various concentrations (5-20 µM) of a factor Xa inhibitor as described herein. Increasing concentrations of Compound A are added in vitro. Following 20 mins of incubation, blood is perfused through the collagen coated capillary (type III collagen, 1600 sec$^{-1}$) as described in Example 4. It is contemplated that increasing concentrations of Compound A in combination with a fixed concentration of a selected factor Xa inhibitor (e.g., rivaroxaban, apixaban) will demonstrate inhibition of thrombosis in a dose-responsive fashion.

Example 12

Combination of Compound A and a Factor Xa Inhibitor in a Thrombin Generation Assay Whole blood from healthy volunteer donors is collected by venipuncture and drawn into 3.2% trisodium citrate (Vacutainer, Becton Dickinson) for anticoagulation. Platelet rich plasma is prepared by centrifugation. In the wells of a 96 well plate, the final platelet count is adjusted to 150,000/μL, platelets are activated by addition of convulxin (100 ng/mL) and incubated at 37° C. for 3 mins. Subsequent to platelet activation, thrombin generation is initiated by addition of 23 pM tissue factor (Innovin, Dade Behring) and 15 mM calcium. Thrombin activity is monitored by cleavage of the specific fluorogenic substrate (Z-gly-gly-arg-AMC, Bachem) in a fluorescence plate reader, as described in Sinha U. et al, Inhibition of purified factor Xa amidolytic activity may not be predictive of inhibition of in vivo thrombosis. Implications for identification of therapeutically active inhibitors. *Arterioscler Thromb Vasc Biol,* 2003, 23:1098-1104.

It is contemplated that similar to Example 5, Compound A in combination with a factor Xa inhibitor (e.g., rivaroxaban, apixaban or other factor Xa inhibitors) will inhibit thrombin production to a greater extent than either compound alone at the same concentration.

Example 13

Combination of Compound A and a Factor Xa Inhibitor Inhibits Thrombosis in a Mouse Mesenteric Artery Model Thrombosis on mouse mesenteric arteries (shear rate 1000-1300 $s^{-1}$) is performed and recorded as previously described with minor modifications, as described in Andre, P. et al., Anticoagulants (thrombin inhibitors) and aspirin synergize with $P2Y_{12}$ receptor antagonism in thrombosis. *Circulation,* 2003, 108(21):2697-703. Platelets are labeled in situ using rhodamine 6G (0.2 mg/mL) administered through the tail vein 10 mins before visualization of the arteries. Vessel-wall injury is triggered by a 1×1-mm filter paper saturated with a 5% $FeCl_3$ solution. After 5 minutes, the filter paper is removed and mesenteric arteries rinsed with warmed saline (37° C.). Platelet vessel-wall interactions are recorded for 40 additional mins or until full occlusion occurs and persists for more than 40 seconds. C57B16J mice are orally gavaged with vehicle control, Compound A (7.5, 20, 60 mg/kg) or betrixaban (4, 40, 400 mg/kg) two hours prior to vascular injury. Thrombosis is analyzed in real time using Simple PCI software, as described in Andre, P. et al., $P2Y_{12}$ regulates platelet adhesion/activation, thrombus growth, and thrombus stability in injured arteries. *J Clin Invest,* 2003, 112(3):398-406. The fluorescence intensity is recorded at a rate of 2 Hz for 40 minutes and plotted over time. Time to occlusion (cessation of blood flow) is analyzed.

Doses of 20 and 60 mg/kg of Compound A prevent occlusion in response to vascular injury over the 40 min observation period. A dose of 7.5 mg/kg delays time to occlusion of the artery. Doses contributing to plasma levels superior to 1 μg/mL of Compound A prevent vascular occlusion, while doses achieving plasma concentration below 1 μg/mL do not prevent occlusion. Doses below 200 ng/mL are non-effective doses. Doses of betrixaban achieving plasma concentrations superior to 1 μg/mL prevent vascular occlusion. Doses below 100 ng/mL are non-effective doses. It is contemplated that when non-effective doses of Compound A and betrixaban are combined, potent synergistic antithrombotic activities will be obtained. Similarly, other factor Xa inhibitors (e.g., rivaroxaban, apixaban) are expected to demonstrate significant antithrombotic activity in the intravital microscopy thrombosis model in mice. It is contemplated that when non-effective doses of rivaroxaban or other factor Xa inhibitors as described herein are combined with non-effective doses of Compound A, potent synergistic antithrombotic activity will be observed.

Example 14

Combination of Compound A and Betrixaban Inhibits Thrombosis in a Mouse Mesenteric Artery Model Thrombosis on mouse mesenteric arteries (shear rate 1000-1300 $s^{-1}$) was performed and recorded as previously described with minor modifications. (Andre, P., et al., *Anticoagulants (thrombin inhibitors) and aspirin synergize with $P2Y_{12}$ receptor antagonism in thrombosis.* Circulation, 2003. 108(21): p. 2697-703.) Platelets were labeled in situ using rhodamine 6G (0.2 mg/mL) administered through the tail vein 10 min before visualization of the arteries. Vessel-wall injury was triggered by a 1×1-mm filter paper saturated with a 10% $FeCl_3$ solution. After 5 minutes, the filter paper was removed and mesenteric arteries rinsed with warmed saline (37° C.). Platelet vessel-wall interactions were recorded for 40 additional min or until full occlusion occurred and persisted for more than 40 seconds. C57B16J mice were orally gavaged with vehicle control, compound A (0.83, 2.5, 7.5, 20, 60 mg/kg) or betrixaban (2, 4, 10 mg/kg) two hours prior to vascular injury. Thrombosis was analyzed in real time using Simple PCI software. (Andre, P., et al., *$P2Y_{12}$ regulates platelet adhesion/activation, thrombus growth, and thrombus stability in injured arteries.* J Clin Invest, 2003. 112(3): p. 398-406.) The fluorescence intensity was recorded at a rate of 2 Hz for 40 minutes and plotted over time. Time to occlusion (cessation of blood flow) is analyzed.

Figure 13:
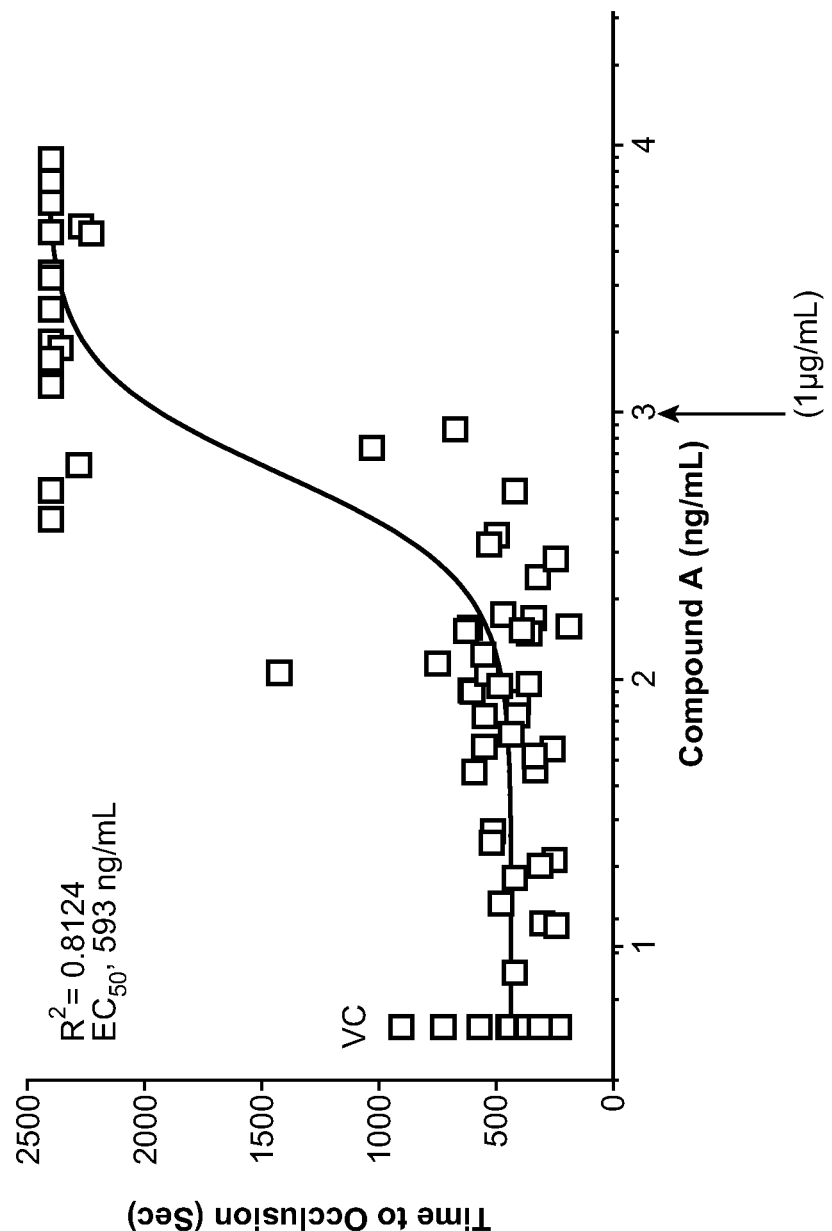
Figure 14:
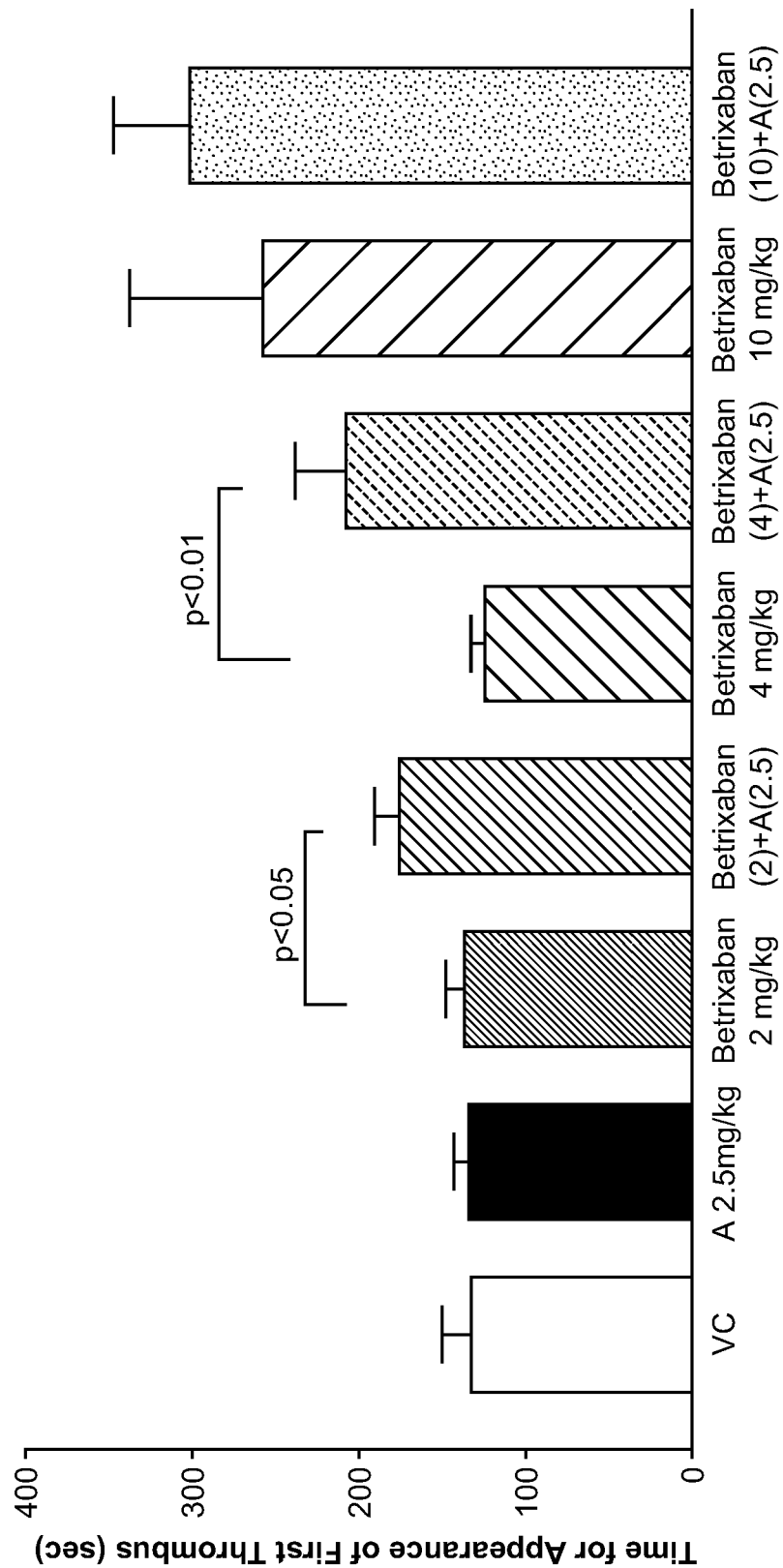
FIGS. 14-17 shows the effect of a combination of Compound A and betrixaban in the same intravital microscopy model.
Figure 15:
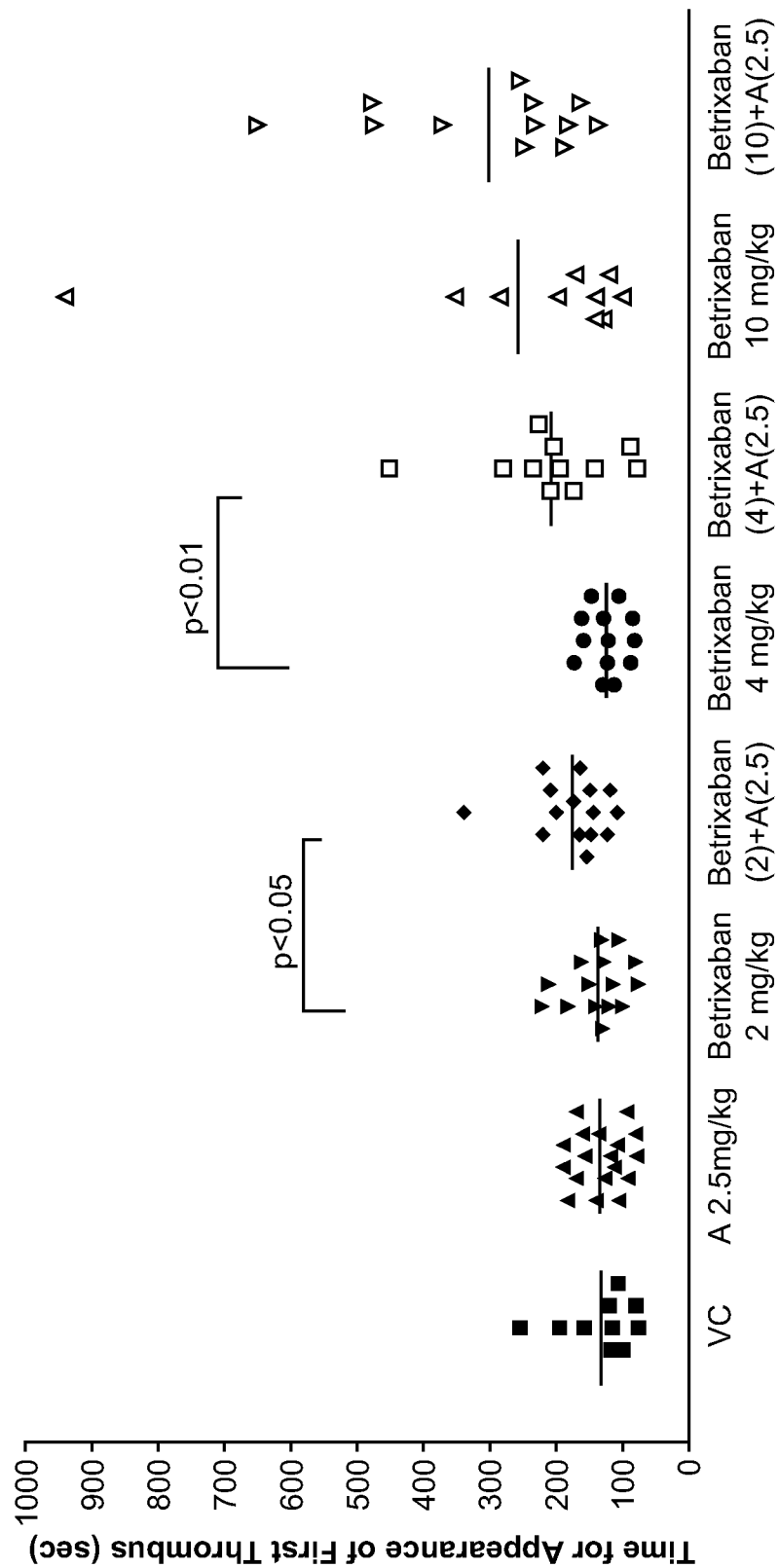
Figure 16:
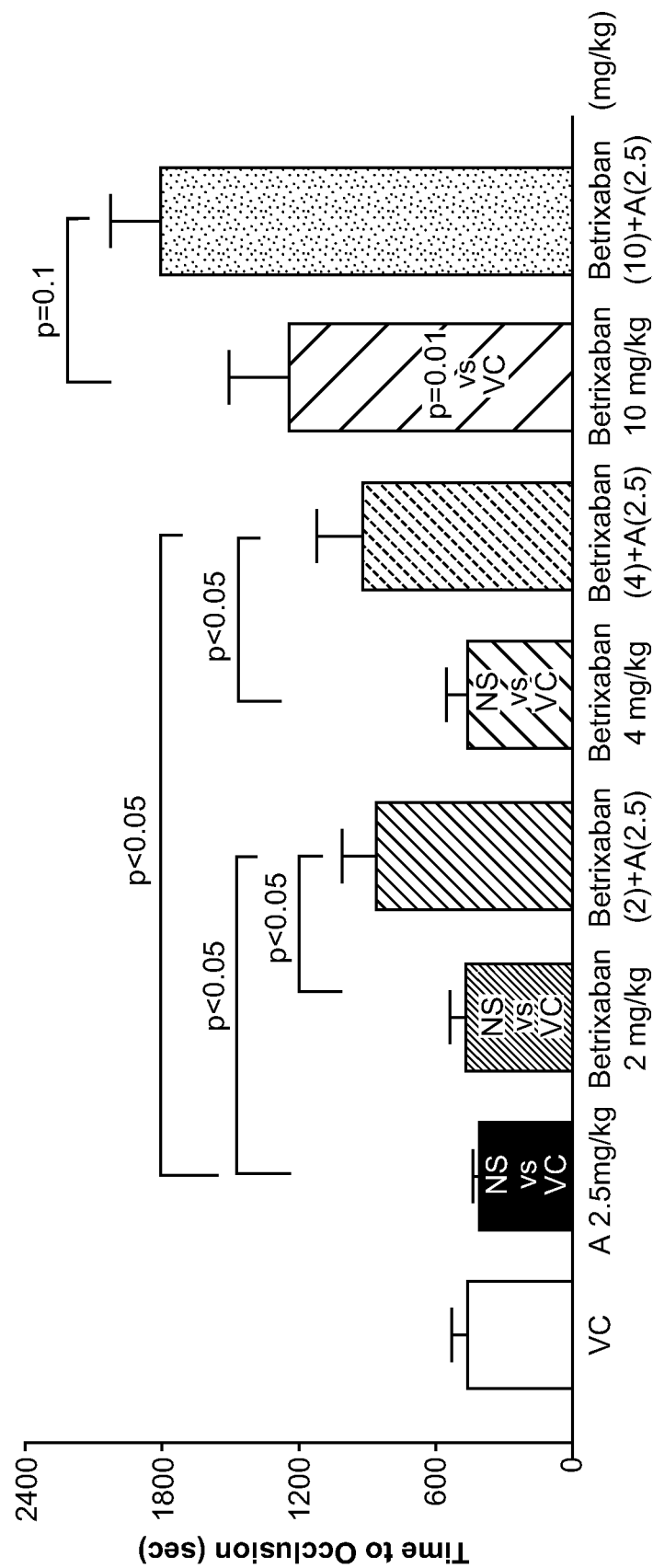
Figure 17:
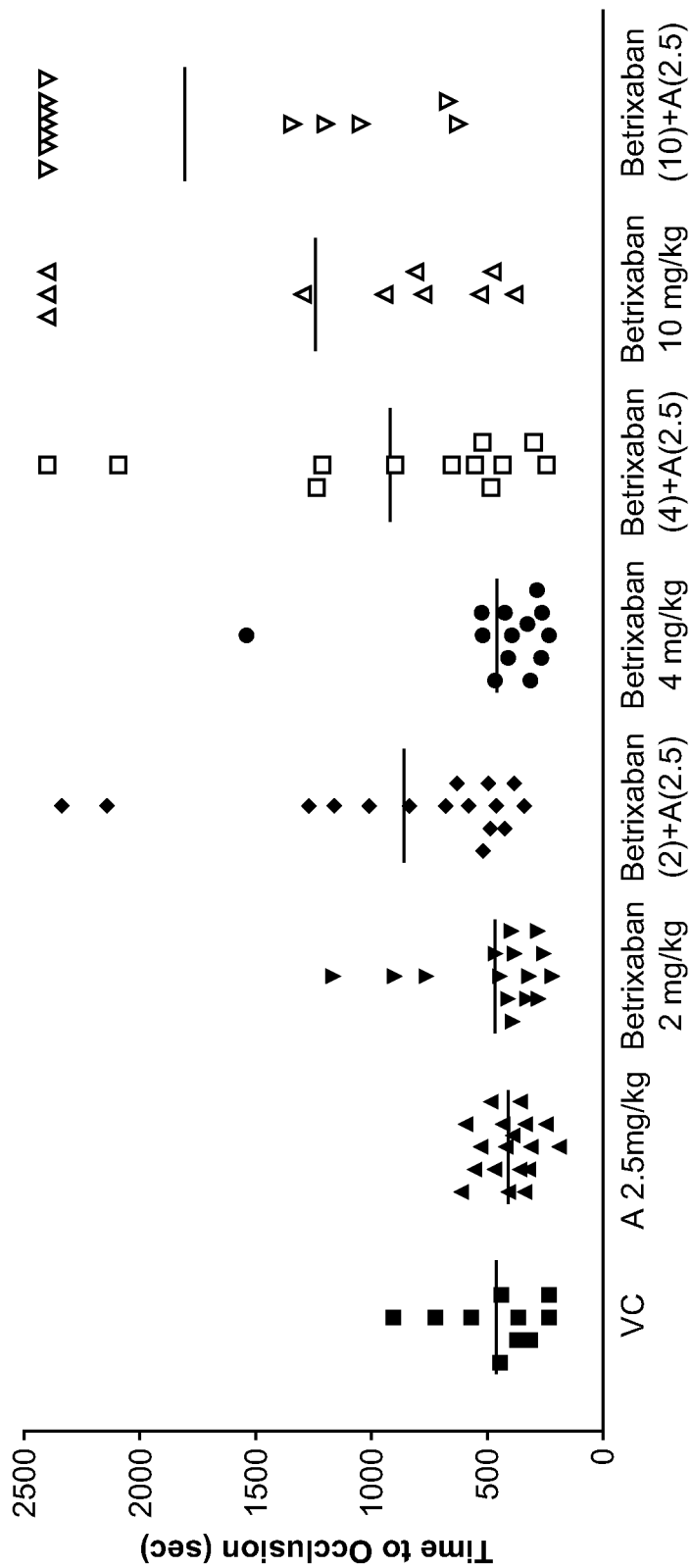

Doses of 0.83 and 2.5 mg/kg Compound A were non-effective in this model. Doses of 7.5, 20 and 60 mg/kg Compound A delayed time for appearance of first thrombus (FIGS. 10-13) and vascular occlusion. Doses of 20 and 60 mg/kg Compound A prevented occlusion in response to vascular injury over the 40 min observation period. Doses contributing to plasma levels superior to 1 μg/mL Compound A prevented vascular occlusion, while doses achieving plasma concentration below 1 μg/mL did not prevent occlusion (FIG. 13). Doses leading to plasma concentrations below 200 ng/mL were non-effective doses in this model (FIG. 13). Doses of 2 and 4 mg/kg betrixaban were non-effective in this model whereas doses of 10 mg/kg betrixaban significantly delayed both time for appearance of first thrombus and time to occlusion (FIGS. 14-17). When non-effective doses of compound A (2.5 mg/kg) and betrixaban (2 and 4 mg/kg) were combined, potent synergistic antithrombotic activities were obtained (FIGS. 14-17).

Plasma concentrations of Compound A and betrixaban were determined on blood draw collected 2 min post-occlusion or 42 min after start of vascular injury.

It is to be understood that while the invention has been described in conjunction with the above embodiments, that the foregoing description and examples are intended to illustrate and not limit the scope of the invention. Other aspects, advantages and modifications within the scope of the invention will be apparent to those skilled in the art to which the invention pertains.

What is claimed is:

1. A method for treating a condition in a mammal characterized by undesired thrombosis comprising administering to said mammal a therapeutically effective amount of the following therapeutic agents:

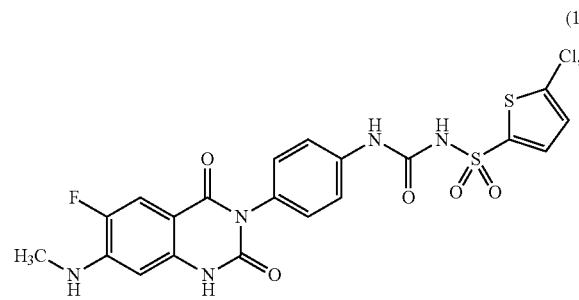

(1)

or a pharmaceutically acceptable salt thereof; and (2) betrixaban or a pharmaceutically acceptable salt thereof.

2. The method according to claim 1, wherein the pharmaceutically acceptable salt of betrixaban is the maleate salt.

3. The method according to claim 1, wherein at least one of the therapeutic agents is administered in a sub-therapeutic dosage.

4. The method according to claim 1, wherein both of the therapeutic agents are administered in sub-therapeutic dosages.

5. The method according to claim 1, wherein the two therapeutic agents are administered simultaneously.

6. The method according to claim 1, wherein the two therapeutic agents are administered sequentially.

7. The method of claim 1, comprising administering to said mammal a therapeutically effective amount of the following three therapeutic agents:

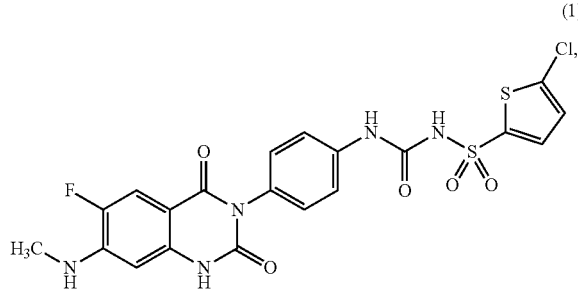 [SMILES: CNc1cc2[nH]c(=O)n(-c3ccc(NC(=O)NS(=O)(=O)c4ccc(Cl)s4)cc3)c(=O)c2cc1F]

(1)

or a pharmaceutically acceptable salt thereof;

(2) an antiplatelet agent; and (3) betrixaban or a pharmaceutically acceptable salt thereof.

8. The method according to claim 7, wherein the pharmaceutically acceptable salt of betrixaban is the maleate salt.

9. The method according to claim 7, wherein at least one of the therapeutic agents is administered in a sub-therapeutic dosage.

10. The method according to claim 7, wherein all of the therapeutic agents are administered in sub-therapeutic dosages.

11. The method according to claim 7, wherein the three therapeutic agents are administered simultaneously.

12. The method according to claim 7, wherein the three therapeutic agents are administered sequentially.

13. The method according to claim 1, wherein the pharmaceutically acceptable salt of

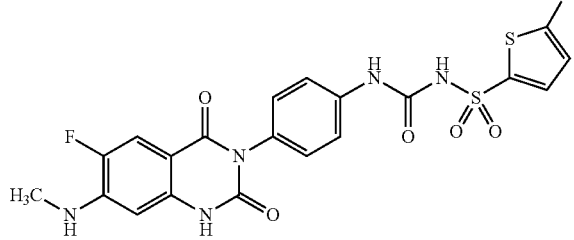

is the potassium salt or sodium salt.

* * * * *